US012409860B2

United States Patent
Xiao

(10) Patent No.: US 12,409,860 B2
(45) Date of Patent: Sep. 9, 2025

(54) AUTONOMOUS DRIVING METHOD, ADS, AND AUTONOMOUS DRIVING VEHICLE

(71) Applicant: Shenzhen Yinwang Intelligent Technologies Co., Ltd., Shenzhen (CN)

(72) Inventor: Zhitao Xiao, Shenzhen (CN)

(73) Assignee: Shenzhen Yinwang Intelligent Technologies Co., Ltd., Shenzhen (CN)

( * ) Notice: Subject to any disclaimer, the term of this patent is extended or adjusted under 35 U.S.C. 154(b) by 204 days.

(21) Appl. No.: 18/183,167

(22) Filed: Mar. 14, 2023

(65) Prior Publication Data

US 2023/0219600 A1 Jul. 13, 2023

Related U.S. Application Data

(63) Continuation of application No. PCT/CN2021/117595, filed on Sep. 10, 2021.

(30) Foreign Application Priority Data

Sep. 17, 2020 (CN) .......................... 202010982543.3

(51) Int. Cl.
*B60W 60/00* (2020.01)
*A61B 5/00* (2006.01)
(Continued)

(52) U.S. Cl.
CPC ....... *B60W 60/0016* (2020.02); *A61B 5/6893* (2013.01); *B60Q 1/46* (2013.01);
(Continued)

(58) Field of Classification Search
None
See application file for complete search history.

(56) References Cited

U.S. PATENT DOCUMENTS

2018/0111628 A1\* 4/2018 Tamagaki ........... B60W 30/143
2019/0121356 A1   4/2019 Migneco et al.
(Continued)

FOREIGN PATENT DOCUMENTS

CN    108032860 A    5/2018
JP    2020063048 A   4/2020
(Continued)

OTHER PUBLICATIONS

"Surface Vehicle Recommended Practice, (R) Taxonomy and Definitions for Terms Related to Driving Automation Systems for On-Road Motor Vehicles," SAE International, J3016™, total 35 pages (Jun. 2018).

*Primary Examiner* — Justin S Lee
(74) *Attorney, Agent, or Firm* — Leydig, Voit & Mayer, Ltd.

(57) ABSTRACT

In an autonomous driving method, a health physiological data range is added to an operational design domain (ODD) deployed on an autonomous driving system (ADS) as an applicable range of the ODD. The ADS receives real-time physiological data of a driver/passenger collected by a monitoring device. When a difference between the real-time physiological data and a health physiological data range is greater than a preset value, and a duration in which the real-time physiological data deviates from the health physiological data range is greater than a first preset duration, the ADS degrades an autonomous driving service being executed by an autonomous driving vehicle, and executing a first driving policy based on the difference and the duration.

18 Claims, 9 Drawing Sheets

*Figure 11 - ODD relative to driving automation levels*

(51) Int. Cl.
*B60Q 1/46* (2006.01)
*G07C 5/00* (2006.01)

(52) U.S. Cl.
CPC ... *B60W 2540/215* (2020.02); *B60W 2540/22* (2013.01); *B60W 2540/221* (2020.02); *B60W 2556/45* (2020.02); *B60W 2720/10* (2013.01); *G07C 5/008* (2013.01)

(56) References Cited

U.S. PATENT DOCUMENTS

2020/0170576 A1    6/2020  Lerner
2022/0346684 A1*  11/2022  Tahara ................ G06V 40/161

FOREIGN PATENT DOCUMENTS

| | | |
|---|---|---|
| JP | 2020122743 A | 8/2020 |
| WO | 2016052507 A1 | 4/2016 |
| WO | 2017221603 A1 | 12/2017 |
| WO | 2019208450 A1 | 10/2019 |
| WO | 2019221240 A1 | 11/2019 |

* cited by examiner

Figure 11 - ODD relative to driving automation levels

AUTONOMOUS DRIVING METHOD, ADS, AND AUTONOMOUS DRIVING VEHICLE

CROSS-REFERENCE TO RELATED APPLICATIONS

This application is a continuation of International Application No. PCT/CN2021/117595, filed on Sep. 10, 2021, which claims priority to Chinese Patent Application No. 202010982543.3, filed on Sep. 17, 2020. The disclosures of the aforementioned priority applications are hereby incorporated by reference in their entirety.

TECHNICAL FIELD

This application relates to the autonomous driving field, and in particular, to an autonomous driving method, an ADS, and an autonomous driving vehicle.

BACKGROUND

Automobiles have experienced more than 100 years of development since invention and have become an indispensable part in people's life. With improvement of living standards, people impose increasingly high requirements on travel comfort, convenience, and the like. As automobiles evolve towards intelligence, autonomous driving technologies emerge.

However, in recent years, accidents frequently occur in autonomous driving cars. For example, on May 7, 2016, a Tesla car with "autonomous driving assistance" enabled crashed into a container truck and the driver died. On the evening of Mar. 18, 2018, a woman in Arizona was injured by an Uber autonomous driving car and died. This causes people's concerns about safety of autonomous driving and forces people to re-examine and think about development of the autonomous driving technologies.

Currently, the autonomous driving classification standard J3016TM of Society of Automotive Engineers (SAE) International is widely used in the industry. This standard is also referred to as Taxonomy and Definitions for Terms Related to Driving Automation System for On-Road Motor Vehicles. This standard defines autonomous driving levels (that is, a total of six autonomous driving levels: L0 to L5) based on a dynamic driving task (DDT), but lacks consideration for driving safety. In view of this, based on a status quo of the existing autonomous driving technologies, an autonomous driving policy that focuses on driving safety, especially for scenarios in which health statuses of drivers/passengers are uncertain, needs to be launched urgently.

SUMMARY

Embodiments of this application provide an autonomous driving method, an ADS, and an autonomous driving vehicle, to newly add a health physiological data range as an applicable range of an operational design domain (ODD) to the ODD. When real-time physiological data of a driver/passenger deviates from the range for a specific duration, an autonomous driving system (ADS) determines that health of the driver/passenger is abnormal, and executes a corresponding first driving policy based on a deviation degree and the duration, to handle a sudden health accident of the driver/passenger in a timely manner, and reduce an occurrence rate of traffic accidents.

In view of this, the following technical solutions are provided in embodiments of this application.

According to a first aspect, an embodiment of this application first provides an autonomous driving method, which can be applied to the autonomous driving field. The method includes: First, a driver/passenger in an autonomous driving vehicle in which an ADS is deployed wears a monitoring device (for example, a smart watch, a smart band, or a smart cardiotachometer, or another wearable device). The monitoring device may collect real-time physiological data of the driver/passenger in real time, and then send these pieces of collected real-time physiological data to the ADS by using a communication protocol (for example, Bluetooth or Wi-Fi). After receiving the real-time physiological data of the driver/passenger that is sent by the monitoring device, the ADS determines whether the real-time physiological data deviates from a health physiological data range. When determining that a difference between the received real-time physiological data and the health physiological data range is greater than a preset value, the ADS further determines whether a duration in which the real-time physiological data deviates from the health physiological data range is greater than a first preset duration. When determining that the duration in which the real-time physiological data deviates from the health physiological data range is greater than the first preset duration, the ADS performs degradation processing on an autonomous driving service that is being executed by the autonomous driving vehicle, and executes a first driving policy based on specific values of the difference and the duration. The health physiological data range is an applicable range added to an ODD in advance. An additional applicable range is used to indicate a health indicator of the driver/passenger, that is, the health physiological data range, for example, a normal heart rate range and a normal blood pressure range, is added to the ODD defined in the autonomous driving classification standard J3016TM. The ODD is deployed on the ADS.

In the implementation of this application, the health physiological data range as the applicable range of the ODD is newly added to the ODD. When the real-time physiological data of the driver/passenger deviates from the range for specific duration, the ADS determines that health of the driver/passenger is abnormal, and executes the corresponding first driving policy based on a deviation degree and the duration, to handle a sudden health accident of the driver/passenger in a timely manner, and reduce an occurrence rate of traffic accidents.

In a possible design of the first aspect, regardless of a specific autonomous driving level, when the real-time physiological data collected by the monitoring device is not restored to fall within the health physiological data range within a second preset duration (for example, within eight minutes), the ADS sends an authorization request to the driver/passenger. The authorization request may be communicated to the driver/passenger in a voice broadcast manner, or may be communicated to the driver/passenger in an interface display manner (with a premise that a display is deployed on the autonomous driving vehicle). This is not specifically limited herein. The authorization request is used to ask the driver/passenger whether a second driving policy needs to be executed. After the driver/passenger receives the authorization request sent by the ADS, the ADS executes the second driving policy when the driver/passenger accepts the authorization request.

In the implementation of this application, the second driving policy is essentially an upgrade of an original risk mitigation strategy. For the original risk mitigation strategy, regardless of a specific autonomous driving level, when the ADS cannot perform a dynamic driving task or the driver/ passenger cannot take over a dynamic driving task, a final objective of the risk mitigation strategy is "stopping the vehicle", that is, only vehicle safety in a narrow sense is considered. However, in embodiments of this application, for the second driving policy, in addition to considering stopping the vehicle, more efforts may be made in the vehicle in an actual situation, including but not limited to measures such as calling for help, organizing a rescue, requesting to arrange an emergency access, and reserving a medical resource.

In a possible design of the first aspect, the second driving policy may be any one or more of the following: stopping on a roadside, calling for a rescue, establishing a communication connection to a medical institution, planning a traveling path between the autonomous driving vehicle and the medical institution, reserving a medical resource, and requesting to arrange an emergency medical treatment channel.

In the implementation of this application, several representation forms of the second driving policy are specifically described, and a requirement of "first aid platinum 10 minutes" is fully considered. In other words, time for discovering a health problem is advanced, so that advance detection and timely handling are implemented. In this way, user experience is desirable, and health of the driver/passenger is ensured. This reduces an occurrence rate of traffic accidents, and also brings huge social benefits.

In a possible design of the first aspect, if an autonomous driving level is L4 or L5, a person in a driving seat of the autonomous driving vehicle does not have a vehicle control right to control the autonomous driving vehicle. In this case, the person cannot be referred to as a driver and is usually referred to as a driver/passenger. Then, that the ADS executes a first driving policy based on the difference and the duration may be specifically: The ADS determines a health level of the driver/passenger based on the difference and the duration. When the ADS determines that the health level is a mild abnormality, the first driving policy may be any one or more of: controlling, by the ADS, the autonomous driving vehicle to decrease a speed to be lower than a preset speed (for example, lower than 60 km/h), travel on a roadside, and turn on a hazard warning signal light.

The implementation of this application describes how the first driving policy is when the health level of the driver/passenger is a mild abnormality if the autonomous driving level is the level L4 or the level L5. To be specific, the health level is determined based on the difference between the real-time physiological data and the health physiological data range and the deviation duration, and different first driving policies are used based on different health levels. This is more pertinent to specific cases.

In a possible design of the first aspect, if the autonomous driving level is the level L4 or the level L5, when the ADS determines that the health level is a severe abnormality, the first driving policy may be any one or more of: controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and unlock a central door lock.

The implementation of this application describes how the first driving policy is when the health level of the driver/passenger is a severe abnormality if the autonomous driving level is the level L4 or the level L5. To be specific, the health level is determined based on the difference between the real-time physiological data and the health physiological data range and the deviation duration, and different first driving policies are used based on different health levels. This is more pertinent to specific cases.

In a possible design of the first aspect, if the autonomous driving level is L3, the driver/passenger is a driver in a driving seat of the autonomous driving vehicle. When the difference between the real-time physiological data and the health physiological data range is greater than the preset value, and the duration in which the real-time physiological data deviates from the health physiological data range is greater than the first preset duration, it indicates that there is a high probability that a health status of the driver/passenger is undesirable in this case. The ADS makes the ADS invariably occupy control permission of the autonomous driving vehicle, that is, the vehicle control right cannot be handed over to the driver/passenger. Then, the ADS further determines a health level of the driver/passenger based on the deviation difference and the deviation duration, and executes the corresponding first driving policy based on the health level. Specifically, when the ADS determines that the health level is a mild abnormality, in addition to making the ADS invariably occupy the control right of the autonomous driving vehicle, the first driving policy may be further any one or more of: controlling, by the ADS, the autonomous driving vehicle to decrease a speed to be lower than a preset speed (for example, lower than 60 km/h), travel on a roadside, and turn on a hazard warning signal light.

The implementation of this application provides the following description: In addition to making the ADS invariably occupy the control right of the autonomous driving vehicle, the first driving policy may be further the any one or more of: controlling, by the ADS, the autonomous driving vehicle to decrease the speed to be lower than the preset speed, travel on the roadside, and turn on the hazard warning signal light, when the health level of the driver/passenger (the driver/passenger is actually the driver in the driving seat in the case of the level L3) is the mild abnormality if the autonomous driving level is L3. To be specific, the health level is determined based on the difference between the real-time physiological data and the health physiological data range and the deviation duration, and different first driving policies are used based on different health levels. This is more pertinent to specific cases. Moreover, in this embodiment of this application, the driver/passenger has a right to take over the vehicle control right only when the health level of the driver/passenger is a normal level; otherwise, the vehicle control right cannot be handed over to the driver/passenger. This avoids a vehicle risk and a personal safety problem caused because the driver/passenger actually has no takeover capability in a specific time period due to a physical health problem.

In a possible design of the first aspect, if the autonomous driving level is the level L3, when the ADS determines that the health level is a severe abnormality, in addition to making the ADS invariably occupy the control right of the autonomous driving vehicle, the first driving policy may be further any one or more of: controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and unlock a central door lock.

The implementation of this application provides the following description: In addition to making the ADS invariably occupy the control right of the autonomous driving vehicle, the first driving policy may be further the any one or more of: controlling the autonomous driving vehicle to slowly decrease the speed to zero, stop on the roadside, turn on the hazard warning signal light, run at the idle speed, turn on the external circulation of the vehicle, turn on the internal circulation of the vehicle, set the in-vehicle target temperature, and unlock the central door lock, when the health level of the driver/passenger (the driver/passenger is actually the driver in the driving seat in the case of the level L3) is the severe abnormality if the autonomous driving level is L3. To be specific, the health level is determined based on the difference between the real-time physiological data and the health physiological data range and the deviation duration, and different first driving policies are used based on different health levels. This is more pertinent to specific cases. Moreover, in this embodiment of this application, the driver/passenger has a right to take over the vehicle control right only when the health level of the driver/passenger is a normal level; otherwise, the vehicle control right cannot be handed over to the driver/passenger. This avoids a vehicle risk and a personal safety problem caused because the driver/passenger actually has no takeover capability in a specific time period due to a physical health problem.

In a possible design of the first aspect, regardless of a specific autonomous driving level, when the real-time physiological data collected by the monitoring device is restored to fall within the health physiological data range within the second preset duration (for example, within eight minutes), it indicates that the health status of the driver/passenger is temporarily restored. In this case, the ADS may control the autonomous driving vehicle to recover a degraded autonomous driving service. For example, it is assumed that the original autonomous driving service that is being executed by the autonomous driving vehicle is "high-speed car-following driving at a speed of 100 km/h", and the difference between the real-time physiological data and the health physiological data range exceeds the preset value for the first preset duration (for example, three minutes). Then, the ADS degrades the autonomous driving service to "high-speed car-following driving at a speed of 60 km/h", and continuously monitors subsequently collected real-time physiological data. If the monitored real-time physiological data is restored to fall within the health physiological data range within the second preset duration (for example, within eight minutes), the ADS restores the degraded "high-speed car-following driving at a speed of 60 km/h" autonomous driving service to the original "high-speed car-following driving at a speed of 100 km/h".

In the implementation of this application, regardless of a specific autonomous driving level (L3, L4, or L5), when the real-time physiological data collected by the monitoring device is restored to fall within the health physiological data range within the second preset duration, it indicates that the health status of the driver/passenger is temporarily restored. In this case, the ADS may control the autonomous driving vehicle to recover the degraded autonomous driving service. This improves user experience.

In a possible design of the first aspect, the ADS may further generate an event log based on the real-time physiological data, where the event log is used to record abnormal real-time physiological data and a series of subsequent operations of the ADS during a period when the real-time physiological data deviates from the health physiological data range; and periodically (for example, every five minutes) report the event log to a cloud server corresponding to the autonomous driving vehicle.

In the implementation of this application, the ADS may record, as the event log, all health-related data and operations during a period when the real-time physiological data is abnormal, and periodically report the event log to the cloud end corresponding to the autonomous driving vehicle for backup. This is convenient to distinguish responsibilities between the person and the vehicle.

In a possible design of the first aspect, the real-time physiological data includes at least one type of the following physiological data: real-time blood pressure, a real-time heart rate, real-time blood oxygen, a real-time body temperature, a premature heartbeat, atrial fibrillation, and other real-time physiological data of the driver/passenger, provided that the physiological data can be collected by the monitoring device and can reflect the health status of the driver/passenger. This is not specifically limited herein.

In the implementation of this application, several common forms of the real-time physiological data are described, and are selective and flexible.

A second aspect of embodiments of this application provides an ADS. The ADS has a function of implementing the method according to any one of the first aspect or the possible implementations of the first aspect. The function may be implemented by using hardware, or may be implemented by hardware executing corresponding software. The hardware or software includes one or more modules corresponding to the function.

A third aspect of embodiments of this application provides an ADS. The ADS may include a memory, a processor, and a bus system. The memory is configured to store a program. The processor is configured to invoke the program stored in the memory, to perform the method according to any one of the first aspect or the possible implementations of the first aspect of embodiments of this application.

A fourth aspect of embodiments of this application provides an autonomous driving vehicle. The autonomous driving vehicle includes a processor and a memory. The memory is configured to store a program. The processor is configured to invoke the program stored in the memory, to perform the method according to any one of the first aspect or the possible implementations of the first aspect of embodiments of this application.

A fifth aspect of this application provides a computer-readable storage medium. The computer-readable storage medium stores instructions. When the instructions are run on a computer, the computer is enabled to perform the method according to any one of the first aspect or the possible implementations of the first aspect.

A sixth aspect of embodiments of this application provides a computer program product. When the computer program product runs on a computer, the computer is enabled to perform the method according to any one of the first aspect or the possible implementations of the first aspect.

A seventh aspect of embodiments of this application provides a chip. The chip includes at least one processor and at least one interface circuit, and the interface circuit is coupled to the processor. The at least one interface circuit is configured to perform a receiving function and a sending function, and send instructions to the at least one processor. The at least one processor is configured to run a computer program or instructions, and has a function of implementing the method according to any one of the first aspect or the possible implementations of the first aspect. The function may be implemented by using hardware, software, or a combination of hardware and software. The hardware or software includes one or more modules corresponding to the function. In addition, the interface circuit is configured to communicate with a module other than the chip.

DESCRIPTION OF EMBODIMENTS

Figure 1:
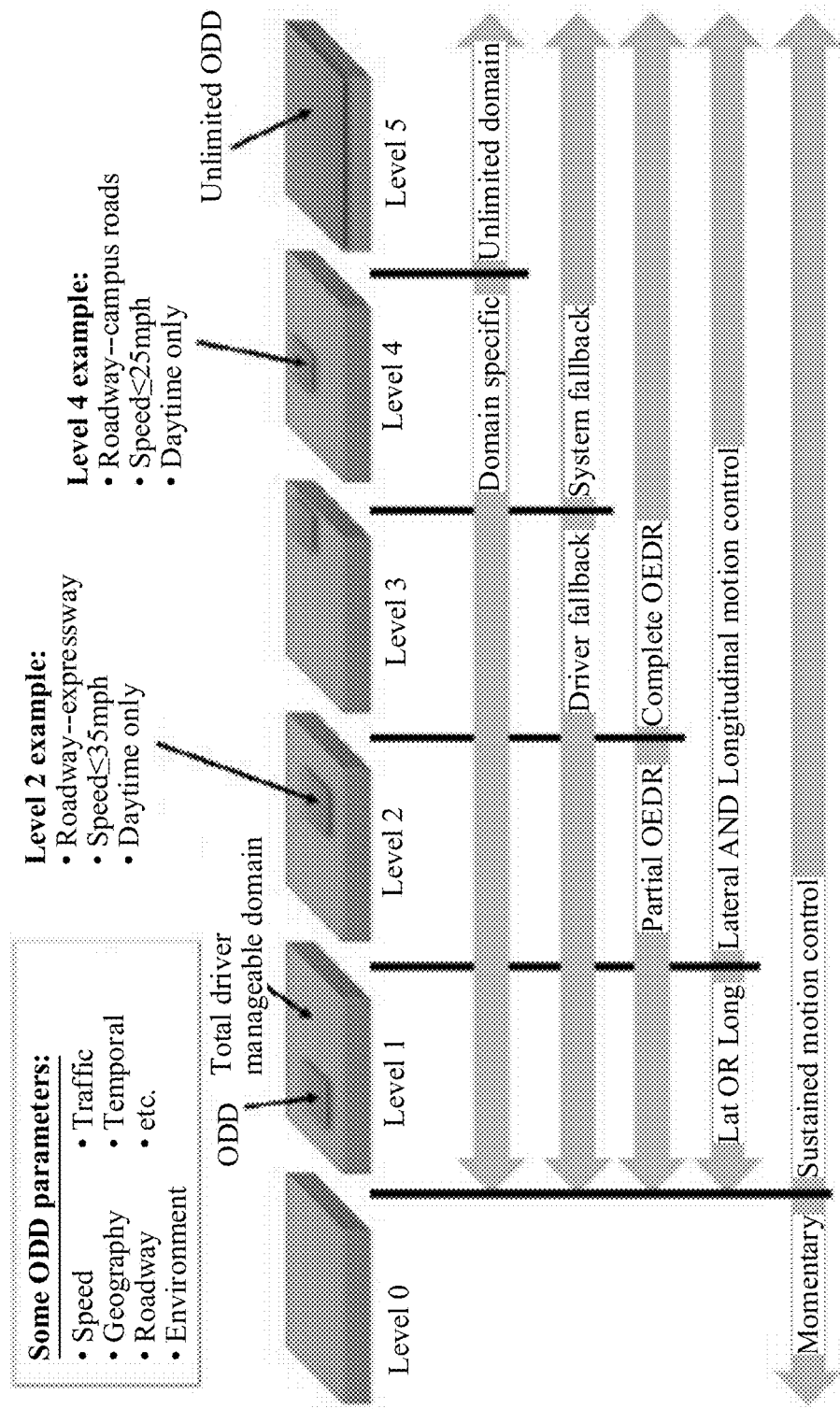
FIG. 1 is a schematic diagram of an ODD defined in FIG. 11 in the chapter 6 of the autonomous driving classification standard J3016TM.

Embodiments of this application provide an autonomous driving method, an ADS, and an autonomous driving vehicle, to newly add a health physiological data range as an applicable range of an ODD to the ODD. When real-time physiological data of a driver/passenger deviates from the range for specific duration, an ADS determines that health of the driver/passenger is abnormal, and executes a corresponding first driving policy based on a deviation degree and the duration, to handle a sudden health accident of the driver/passenger in a timely manner, and reduce an occurrence rate of traffic accidents.

In the specification, claims, and accompanying drawings of this application, terms such as "first" and "second" are intended to distinguish between similar objects but do not necessarily indicate a specific order or sequence. It should be understood that the terms used in such a way are interchangeable in proper circumstances, which is merely a discrimination manner that is used when objects having a same attribute are described in embodiments of this application. In addition, terms "include", "contain", and any other variants are intended to cover a non-exclusive inclusion, so that a process, method, system, product, or device that includes a series of units is not necessarily limited to those units, but may include other units not expressly listed or inherent to such a process, method, product, or device.

Embodiments of this application relate to a lot of related knowledge about autonomous driving. For better understanding of the solutions in embodiments of this application, the following first describes related terms and concepts that may be used in embodiments of this application. It should be understood that interpretations of related concepts may be limited because of specific situations of embodiments of this application, but this does not mean that this application can only be limited to the specific situations. There may be a difference between specific situations of different embodiments. Details are not limited herein.

(1) Automated Driving System (ADS)

The ADS is a system including both hardware and software that implement driving automation, and may also be referred to as a control system. A vehicle in which the ADS is deployed is referred to as an autonomous driving vehicle, or may be referred to as a driverless car, a computer driving car, a wheeled mobile robot, or the like. Under the control of the ADS, the autonomous driving vehicle implements interaction and sharing between traffic participants by configuring advanced apparatuses such as a vehicle-mounted sensor, a controller, a data processor, and an executor and by using modern mobile communication and network technologies such as an Internet of vehicles, 5G, and V2X. In this way, the autonomous driving vehicle has functions such as sensing and perception, decision-making and planning, and control and execution in complex environments.

Under the control of ADS, an entire working process of the autonomous driving vehicle is as follows: First, an external environment is sensed and identified by using a radar, a laser radar, a camera, an in-vehicle network system, and the like, to obtain perception information of the external environment. Then, based on fused multi-faceted perception information, an intelligent algorithm is used to learn external scenario information, predict a track of a traffic participant in a scenario, and plan a running track of the vehicle. Finally, a track target obtained through decision-making and planning is tracked, traveling actions such as controlling a throttle, braking, and steering of the vehicle are implemented, and a traveling speed, a location, a direction, and other statuses of the vehicle are adjusted, to ensure safety, maneuverability, and stability of the vehicle.

(2) Operational Design Domain (ODD)

The ODD may also be referred to as a design running domain, a design applicable domain, a design traveling area, or the like. The ODD refers to safe working environments of an autonomous driving vehicle, is essentially a set of parameters, and is a condition and an application range (that is, an application range of autonomous driving) in which an ADS is designed to take effect.

Specifically, information such as a weather environment, a road condition (for example, a radius of a straight road or a curve road), a vehicle speed, and a traffic flow is measured, to ensure that a capability of a system is kept in a safe environment. The ODD can be understood as safe working environments of the autonomous driving vehicle, including a speed (a high speed, a low speed, or the like), a terrain (a plain, a mountain, or the like), a road surface condition (a straight road, a curve road, or the like), an environment (weather, a climate, an infrastructure, and the like), traffic conditions (simple or complex, a violation behavior, route fixation, and the like), a time period (in the daytime or at nighttime), and the like. A series of conditions, for example, at a high speed or a low speed, in a plain or a mountain, on a straight road or a curve road, weather conditions, infrastructure conditions, whether traffic conditions are simple or complex, and in the daytime or at nighttime, play a decisive role in performance of autonomous driving. FIG. 1 shows an ODD defined in FIG. 11 in the chapter 6 of the autonomous driving classification standard J3016TM. Considered elements include a vehicle speed, a terrain, a road type, a weather environment, traffic conditions, time, and the like. Running conditions that ODDs corresponding to different autonomous driving levels need to satisfy may be different. As shown in FIG. 1, elements that need to be satisfied by a running condition of an ODD corresponding to a level 2

(that is, a level L2) are: daytime, an expressway, and a vehicle speed less than or equal to 35 miles per hour (unit: mph); and elements that need to be satisfied by a running condition of an ODD corresponding to a level 4 (that is, a level L4) are: daytime, a campus road, and a vehicle speed less than or equal to 25 mph.

Whether an ODD is comprehensive and detailed can reflect, to some extent, whether an autonomous driving solution is mature. Whether conditions that are set for the ODD are strict can also reflect, to some extent, levels of solutions at a same class. If the vehicle can be used only within a strictly restricted range, an "intelligent" degree of the vehicle may be lower, actual application scenarios are fewer, and experience is poorer.

Figure 2:
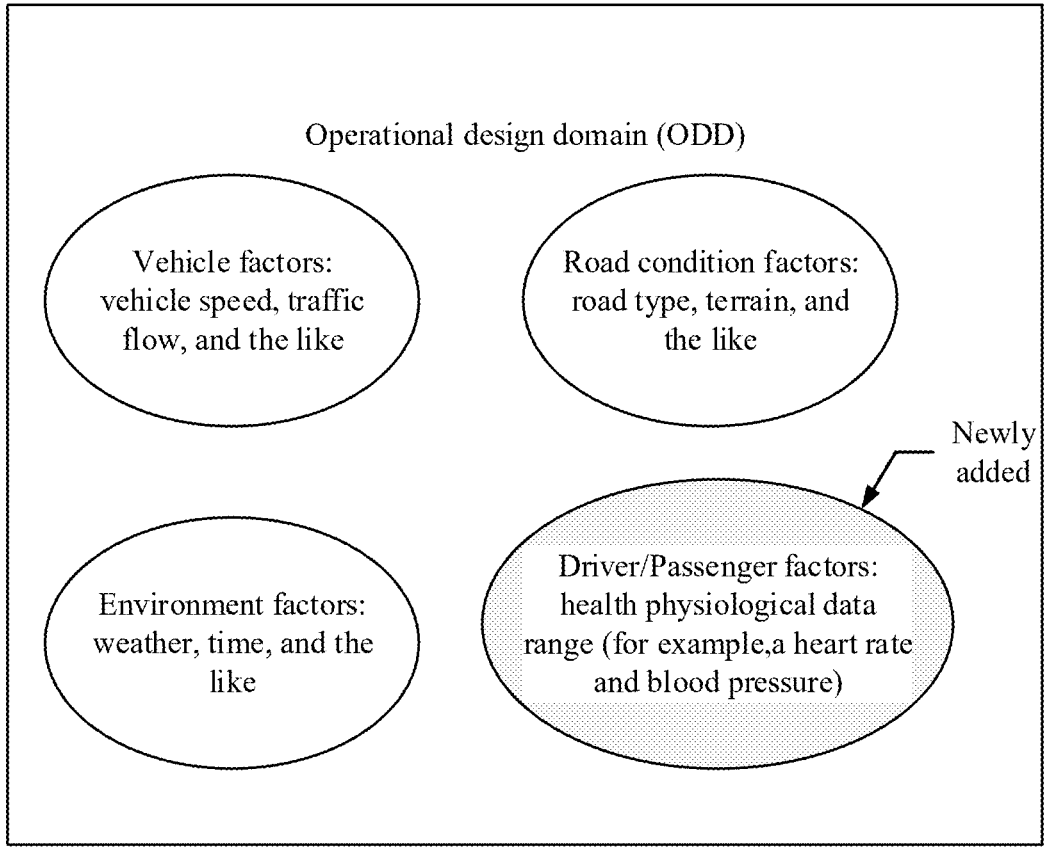
FIG. 2 is a schematic diagram of an additional applicable range used to indicate a health indicator of a driver/passenger is added to a defined ODD according to an embodiment of this application.

It should be noted that in embodiments of this application, as shown in FIG. 2, an additional applicable range used to indicate a health indicator of a driver/passenger, that is, a health physiological data range, for example, a normal heart rate range and a normal blood pressure range, is added to the ODD defined in the autonomous driving classification standard J3016TM. This can avoid a vehicle risk caused because a vehicle takeover person actually has no takeover capability in a specific time period due to a physical health problem. The newly added health physiological data range may be added to an ODD at each autonomous driving level, and in particular, needs to be added to ODDs at levels L3 to L5. Specifically, in an autonomous driving service related to the autonomous driving level L3, the ODD is integrated with the health indicator of the driver/passenger (a driver/passenger at the level L3 is a driver), that is, considers a driver takeover capability. In autonomous driving services related to the autonomous driving levels L4 and L5, the driver/passenger has no takeover obligation or approach, and corresponding ODDs also need to be integrated with the health indicator of the driver/passenger to guide the ADS to execute a subsequent risk mitigation strategy.

(3) Operational Design Condition (ODC)

The ODC is conditions in which a driving automation function can work normally and that is determined during design operation, including setting an ODD, a driver status, and other necessary conditions.

(4) Dynamic Driving Task (DDT)

The dynamic driving task refers to all real-time operations and policy functions (decision-making behaviors) that are needed by a vehicle for traveling on a road, and does not include strategic functions such as journey arrangement and selection of a destination and passed places. Specifically, the DDT refers to operations and decision-making that are needed by the vehicle for traveling on the road, including performing operations in a horizontal motion direction and a vertical motion direction on the vehicle, monitoring a surrounding environment of the vehicle, performing a corresponding operation for the surrounding environment, and the like. In brief, the dynamic driving task can be understood as several specific functions implemented in the autonomous driving solution. Common car-following driving, adaptive cruise, emergency braking in existing mass-produced assisted driving and autonomous driving vehicles, and driver confirmed lane change and proactive overtaking equipped in few vehicles are typical dynamic driving tasks.

(5) Dynamic Driving Task Fallback (DDT Fallback)

During design of autonomous driving, a systematic failure (that is, a fault that causes a system to fail in work) or a situation beyond an original operational design domain of the system needs to be considered. When the two cases occur, a solution for minimizing risks needs to be provided. In an existing mass production solution, hierarchical warning is a common dynamic driving task fallback operation. Although minimal risk conditions designed by vendors differ from each other, deceleration to stop is a common and universal design.

A Nullmax solution is used as an example. When detecting that a driver needs to take over a vehicle, the system hierarchically sends a takeover prompt. If the driver does not respond to a level-1 prompt in a specified time period, the system sends a level-2 prompt whose strength is fully upgraded. If the vehicle is not taken over in the specified time period yet, the vehicle enters a minimal risk condition, decreases a vehicle speed, and then stops.

(6) Risk Mitigation Strategy (RMS)

The RMS is risk reduction measures taken by an ADS, for example, stopping in a lane, when the ADS cannot carry out a dynamic driving task or a driver/passenger cannot take over a dynamic driving task.

Specifically, the following content is defined in the section 8.6 of the autonomous driving classification standard J3016TM: A vehicle provided with levels L2/L3 autonomous driving characteristics may have an additional failure mitigation strategy (namely, a risk mitigation strategy), regardless of what occurs on the vehicle (a driver cannot control an L2 autonomous driving characteristic in the case of L2, or a vehicle takeover person cannot take over the vehicle in the case of L3). The strategy controls the vehicle to stop. A vehicle provided with levels L4/L5 autonomous driving characteristics also has a similar failure mitigation strategy. When the ADS exits because of a rare disaster-induced failure, the ADS controls the vehicle to slow down until the vehicle stops before exiting. In other words, regardless of a specific autonomous driving level, when the ADS cannot perform the dynamic driving task or the driver/passenger cannot take over the dynamic driving task, a final objective of the risk mitigation strategy is "stopping the vehicle".

(7) Minimal Risk Condition (MRC)

When a vehicle cannot complete a scheduled journey, a driver/passenger or an ADS goes on the journey and finally makes an accident risk of the vehicle acceptable.

(8) Automated Driving Classification Standard J3016TM

Figure 3:
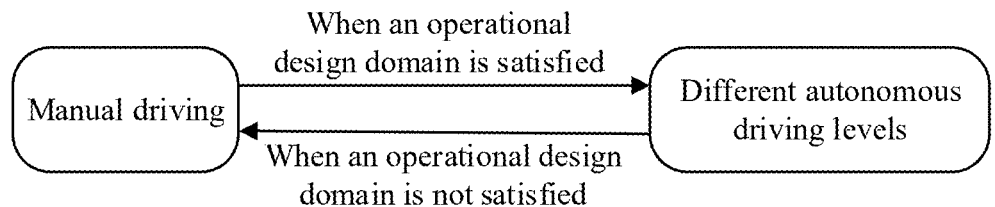
FIG. 3 is a schematic diagram of a relationship between different autonomous driving levels and manual driving according to an embodiment of this application.

Based on degrees to which a driver/passenger and a vehicle intervene in the vehicle during traveling, the autonomous driving classification standard J3016TM defines six levels of autonomous driving technologies: a level 0, a level 1, a level 2, a level 3, a level 4, and a level 5, which may also be referred to as L0, L1, L2, L3, L4, and L5 for short. As shown in FIG. 3, the autonomous driving classification standard J3016TM proposes that an ODD is a sufficient condition for satisfying different autonomous driving levels. When an operational design condition corresponding to the ODD is satisfied, an ADS can implement autonomous driving corresponding to an autonomous driving level. When an operational design condition corresponding to the ODD is not satisfied, only manual driving by a driver can be performed.

Specifically, a relationship between autonomous driving levels and corresponding classification elements is described in Table 1. A system in Table 1 is an ADS. Herein, all autonomous driving levels are described as follows:

A level L0 is also referred to as emergency assistance. A driver fully controls a vehicle without any proactive safety configuration. Currently, vehicles at this autonomous driving level almost disappear from the market.

A level L1 is also referred to as partial driving assistance. In some cases, an ADS can assist a driver in completing some driving tasks.

A level L2 is also referred to as combined driving assistance. At L2, an ADS can complete some driving tasks, but a driver needs to monitor a driving environment and take over a vehicle at any time when a problem occurs. At this autonomous driving level, the driver can rectify erroneous perception and judgment of the ADS at any time. Currently, most automobile enterprises can provide ADSs at the level L2. At the level L2, traffic scenarios may be classified into different application scenarios based on speeds and environments, such as a low-speed traffic jam on a ring road, fast driving on an expressway, and automatic parking by a driver in a vehicle.

A level L3 is also referred to as conditional autonomous driving. At L3, an ADS can complete some driving tasks and can monitor a driving environment in some cases. In other words, the ADS needs to be capable of controlling a vehicle to complete all dynamic driving tasks within a specified ODD, but a driver needs to get ready to re-obtain a vehicle control right. Specifically, when the ADS fails or goes beyond the ODD domain corresponding to the autonomous driving level, the ADS sends control permission handover request. The autonomous driving classification standard J3016TM also defines as follows: The ADS can continue to control the vehicle for several seconds after sending the control right handover request, and this time period is used by the driver to get ready to take over the vehicle control right. For example, the driver's hand is placed on a steering wheel, and the driver's eyes look directly in front of the vehicle. The ADS may detect, by using a capacitive steering wheel, whether the driver's hand is placed on the steering wheel, detect, by using a monitoring camera in a driving seat of the vehicle, whether the driver's eyes look at a road, and the like, to determine whether the driver gets ready to take over the vehicle. If the ADS determines that the driver gets ready to take over the vehicle, the ADS hands over the vehicle control right to the driver. Therefore, at this autonomous driving level, the driver is still unallowable to sleep or take a deep rest.

A level L4 may also be referred to as highly autonomous driving. In some environments and specific conditions, an ADS can complete a driving task and monitor a driving environment. In other words, the ADS needs to be capable of completing a dynamic driving task within an ODD and handling a system failure, without intervention by a driver/passenger (because a vehicle at the level L4 needs no driver, there is no driver and only the driver/passenger is involved at this autonomous driving level). Currently, autonomous driving at the level L4 is mainly used in cities, and may provide fully autonomous valet parking or may be directly combined with a taxi hailing service. At this autonomous driving level, within the corresponding ODD domain, all driving-related tasks are unrelated to the driver/passenger, and the ADS is wholly responsible for sensing an external world.

A level L5 may also be referred to as fully autonomous driving. An ADS can complete all driving tasks in all conditions, that is, implement unmanned driving in all working conditions. There is no need to define an ODD, and the ADS can complete all dynamic driving tasks and process all dynamic driving task fallbacks.

TABLE 1

Relationship between autonomous driving levels and corresponding classification elements

| Level | Name | Horizontal and vertical motion control for a vehicle | Target and event detection and response | Dynamic driving task takeover | Operational design domain |
|---|---|---|---|---|---|
| Level L0 | Emergency assistance | Driver | Driver and system | Driver | Limited |
| Level L1 | Partial driving assistance | Driver and system | Driver and system | Driver | Limited |
| Level L2 | Combined driving assistance | System | Driver and system | Driver | Limited |
| Level L3 | Conditional autonomous driving | System | System | Dynamic driving task takeover user (becoming a driver after a takeover) | Limited |
| Level L4 | Highly Autonomous driving | System | System | System | Limited |
| Level L5 | Fully autonomous driving | System | System | System | Not limited* |

*Eliminate restrictions such as commercial and legal factors (9) Driver/Passenger In embodiments of this application, the driver/passenger is essentially a person in a driving seat of an autonomous driving vehicle. When an autonomous driving level is L3 or a lower autonomous driving level, the driver/passenger may also be referred to as a driver in this case, and in some driving tasks, has a vehicle control right to control the autonomous driving vehicle. However, when an autonomous driving level is L4 or L5, the person in the driving seat of the autonomous driving vehicle does not have a vehicle control right to control the autonomous driving vehicle. In this case, the person cannot be referred to as a driver and is usually referred to as a driver/passenger. Therefore, the driver/passenger is a driver at the level L3 or below and is a driver/passenger at the level L4 or the level L5 in this embodiment of this application, and is collectively referred to as a driver/passenger in embodiments of this application.

The following describes embodiments of this application with reference to accompanying drawings. A person of ordinary skill in the art can know that, as technologies develop and a new scenario emerges, the technical solutions provided in embodiments of this application are also applicable to similar technical issues.

Figure 4:
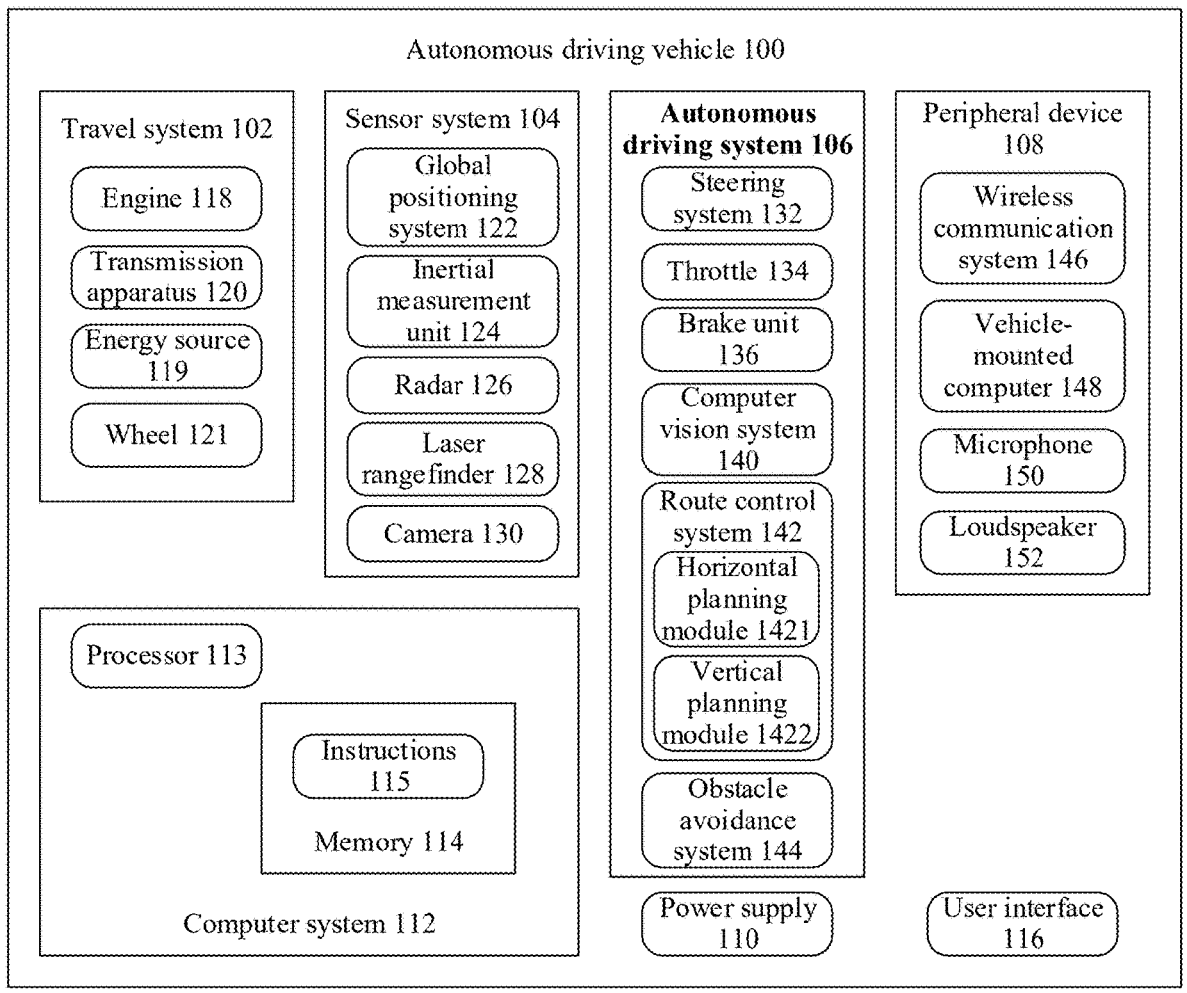
FIG. 4 is a schematic diagram of a structure of an autonomous driving vehicle according to an embodiment of this application.

For better understanding of the solutions, embodiments of this application first describe specific functions of internal structures of an autonomous driving vehicle. FIG. 4 is a schematic diagram of a structure of an autonomous driving vehicle according to an embodiment of this application. The autonomous driving vehicle 100 is configured in a fully or partially autonomous driving mode. For example, the autonomous driving vehicle 100 can control itself when in an autonomous driving mode, and through manual operations, can determine current statuses of the vehicle 100 and a surrounding environment of the vehicle, determine a possible behavior of at least one another vehicle in the surrounding environment, determine a confidence level corresponding to a possibility that the another vehicle performs the possible behavior, and control the autonomous driving vehicle 100 based on the determined information. When the autonomous driving vehicle 100 is in the autonomous driving mode, the autonomous driving vehicle 100 may be alternatively set to operate without interaction with a person.

The autonomous driving vehicle 100 may include various subsystems, such as a travel system 102, a sensor system 104 (for example, a camera, a SICK, an IBEO, a laser radar, and the like in FIG. 3 all belong to modules in the sensor system 104), an autonomous driving system 106, one or more peripheral devices 108, a power supply 110, a computer system 112, and a user interface 116. Optionally, the autonomous driving vehicle 100 may include more or fewer subsystems, and each subsystem may include a plurality of components. In addition, the subsystems and the components of the autonomous driving vehicle 100 may be interconnected in a wired or wireless manner.

The travel system 102 may include components that provide kinetic motion for the autonomous driving vehicle 100. In an embodiment, the travel system 102 may include an engine 118, an energy source 119, a transmission apparatus 120, and a wheel/tire 121.

The engine 118 may be a combination of an internal combustion engine, a motor, an air compression engine, or another type of engine, for example, a hybrid engine formed by a gasoline engine and a motor, or a hybrid engine formed by an internal combustion engine and an air compression engine. The engine 118 converts the energy source 119 into mechanical energy. For example, the energy source 119 includes gasoline, diesel, another oil-based fuel, propane, another compressed-gas-based fuel, anhydrous alcohol, a solar panel, a battery, and another power source. The energy source 119 may also provide energy for another system of the autonomous driving vehicle 100. The transmission apparatus 120 may transmit the mechanical power from the engine 118 to the wheel 121. The transmission apparatus 120 may include a gearbox, a differential gear, and a drive shaft. In an embodiment, the transmission apparatus 120 may further include another component, for example, a clutch. The drive shaft may include one or more shafts that may be coupled to one or more wheels 121.

The sensor system 104 may include several sensors that sense information about the surrounding environment of the autonomous driving vehicle 100. For example, the sensor system 104 may include a positioning system 122 (the positioning system may be a global positioning system GPS, or may be a BeiDou system or another positioning system), an inertial measurement unit (IMU) 124, a radar 126, a laser rangefinder 128, and a camera 130. The sensor system 104 may further include sensors (for example, an in-vehicle air quality monitor, a fuel gauge, and an oil temperature gauge) of an internal system of the monitored autonomous driving vehicle 100. Sensor data from one or more of these sensors may be used to detect an object and corresponding characteristics (a location, a shape, a direction, a speed, and the like) of the object. Such detection and identification are key functions of a safe operation of the autonomous driving vehicle 100. In this embodiment of this application, a laser sensor is a quite important sensing module in the sensor system 104.

The positioning system 122 may be configured to estimate a geographical location of the autonomous driving vehicle 100. In this embodiment of this application, the laser sensor may be used as one of positioning systems 122 to implement precise positioning of the autonomous driving vehicle 100. The IMU 124 is configured to sense changes in a location and an orientation of the autonomous driving vehicle 100 based on an inertial acceleration. In an embodiment, the IMU 124 may be a combination of an accelerometer and a gyroscope. The radar 126 may use a radio signal to sense an object in the surrounding environment of the autonomous driving vehicle 100, and may be specifically represented as a millimeter-wave radar or a laser radar. In some embodiments, in addition to sensing the object, the radar 126 may be further configured to sense a speed and/or an advancing direction of the object. The laser rangefinder 128 may use laser light to sense an object in an environment in which the autonomous driving vehicle 100 is situated. In some embodiments, the laser rangefinder 128 may include one or more laser sources, a laser scanner, one or more detectors, and other system components. The camera 130 may be configured to capture a plurality of images of the surrounding environment of the autonomous driving vehicle 100. The camera 130 may be a still camera or a video camera.

The autonomous driving system 106 controls operations of the autonomous driving vehicle 100 and the components of the autonomous driving vehicle 100. Therefore, in this embodiment of this application, the autonomous driving system 106 may also be referred to as a control system. The autonomous driving system 106 may include various components, such as a steering system 132, a throttle 134, a brake unit 136, a computer vision system 140, a route control system 142, and an obstacle avoidance system 144.

The steering system 132 may be operated to adjust an advancing direction of the autonomous driving vehicle 100. For example, in an embodiment, the steering system 132 may be a steering wheel system. The throttle 134 is configured to control an operation speed of the engine 118 and then control a speed of the autonomous driving vehicle 100. The brake unit 136 is configured to control the autonomous driving vehicle 100 to decelerate, and the brake unit 136 may use friction force to retard the wheel 121. In another embodiment, the brake unit 136 may convert kinetic energy of the wheel 121 into a current. The brake unit 136 may alternatively slow down a rotational speed of the wheel 121 in another form to control the speed of the autonomous driving vehicle 100. The computer vision system 140 may be operated to process and analyze the images captured by the camera 130, to identify the object and/or characteristics in the surrounding environment of the autonomous driving vehicle 100. The object and/or characteristics may include traffic signals, road boundaries, and obstacles. The computer vision system 140 may use an object recognition algorithm, a structure from motion (SFM) algorithm, video tracking, and other computer vision technologies. In some embodiments, the computer vision system 140 may be configured to: draw a map for an environment, track an object, estimate a speed of the object, and the like. The route control system 142 is configured to determine a traveling route and a traveling speed for the autonomous driving vehicle 100. In some embodiments, the route control system 142 may include a horizontal planning module 1421 and a vertical planning module 1422. The horizontal planning module 1421 and the vertical planning module 1422 are configured to determine the traveling route and the traveling speed for the autonomous driving vehicle 100 based on data from the obstacle avoidance system 144, the GPS 122, and one or more predetermined maps. The obstacle avoidance system 144 is configured to identify, evaluate, and avoid or otherwise to bypass obstacles in the environment in which the autonomous driving vehicle 100 is situated. The obstacles may be specifically represented as an actual obstacle and a virtual moving object that may collide with the autonomous driving vehicle 100. In an example, the autonomous driving system 106 may additionally or alternatively include components other than those shown and described. Alternatively, some of the components shown above may be removed from the autonomous driving system 106.

The autonomous driving vehicle 100 interacts with an external sensor, another vehicle, another computer system, or a user by using the peripheral device 108. The peripheral device 108 may include a wireless communication system 146, a vehicle-mounted computer 148, a microphone 150, and/or a loudspeaker 152. In some embodiments, the peripheral device 108 provides a means for the user of the autonomous driving vehicle 100 to interact with the user interface 116. For example, the vehicle-mounted computer 148 may provide information for the user of the autonomous driving vehicle 100. The user interface 116 may further receive a user input by operating the vehicle-mounted computer 148, and the vehicle-mounted computer 148 can be operated by using a touchscreen. In another case, the peripheral device 108 may provide a means for the autonomous driving vehicle 100 to communicate with another in-vehicle device. For example, the microphone 150 may receive audio (for example, a voice command or another audio input) from the user of the autonomous driving vehicle 100. Similarly, the loudspeaker 152 may output audio to the user of the autonomous driving vehicle 100. The wireless communication system 146 may wirelessly communicate with one or more devices directly or through a communication network. For example, the wireless communication system 146 may use 3G cellular communication such as CDMA, EVDO, and GSM/GPRS, 4G cellular communication such as LTE, or 5G cellular communication. The wireless communication system 146 may perform communication by using a wireless local area network (WLAN). In some embodiments, the wireless communication system 146 may directly communicate with a device by using an infrared link, Bluetooth, or ZigBee. Other wireless protocols such as various vehicle communication systems, for example, the wireless communication system 146, may include one or more dedicated short-range communication (DSRC) devices. These devices may include vehicles and/or apparatuses at roadside stations that perform public and/or private data communication with each other.

The power supply 110 may supply power to the components of the autonomous driving vehicle 100. In an embodiment, the power supply 110 may be a rechargeable lithium-ion or lead-acid battery. One or more battery packs of such a battery may be configured as the power supply to supply power to the components of the autonomous driving vehicle 100. In some embodiments, the power supply 110 and the energy source 119 may be implemented together, as in some pure-electric vehicles.

Some or all of functions of the autonomous driving vehicle 100 are controlled by the computer system 112. The computer system 112 may include at least one processor 113, and the processor 113 executes instructions 115 stored in, for example, a non-transient computer-readable medium such as a memory 114. The computer system 112 may be alternatively a plurality of computing devices that control, in a distributed manner, individual components or subsystems of the autonomous driving vehicle 100. The processor 113 may be any conventional processor, for example, a commercially available central processing unit (CPU). Alternatively, the processor 113 may be a dedicated device, for example, an application-specific integrated circuit (ASIC) or another hardware-based processor. Although FIG. 4 functionally illustrates the processor, the memory, and other components of the computer system 112 in a same block, a person of ordinary skill in the art should understand that the processor or the memory may actually include a plurality of processors or memories that are not be stored in a same physical housing. For example, the memory 114 may be a hard disk drive or another storage medium located in a housing different from that of the computer system 112. Therefore, it is understood that a reference to the processor 113 or the memory 114 includes a reference to a set of processors or memories that may or may not operate in parallel. Different from using a single processor to perform the steps described herein, some components such as a steering component and a deceleration component may include respective processors. The processor performs only computation related to a component-specific function.

In various aspects described herein, the processor 113 may be located far away from the autonomous driving vehicle 100 and wirelessly communicate with the autonomous driving vehicle 100. In other aspects, some processes described herein are performed on the processor 113 disposed inside the autonomous driving vehicle 100, while others are performed by a remote processor. The processes include necessary steps for performing a single operation.

In some embodiments, the memory 114 may include the instructions 115 (for example, program logic), and the instructions 115 may be executed by the processor 113 to perform various functions of the autonomous driving vehicle 100, including those functions described above. The memory 114 may also include additional instructions, including instructions to send data to, receive data from, interact with, and/or control one or more of the travel system 102, the sensor system 104, the autonomous driving system 106, and the peripheral device 108. In addition to the instructions 115, the memory 114 may also store data such as road maps, route information, a location, direction, and speed of the vehicle, data of other vehicles of this type, and other information. These pieces of information may be used by the autonomous driving vehicle 100 and the computer system 112 during operation of the autonomous driving vehicle 100 in an autonomous mode, a semi-autonomous mode, and/or a manual mode. The user interface 116 is configured to provide information for or receive information from the user of the autonomous driving vehicle 100. Optionally, the user interface 116 may be included in one or more input/output devices in a set of the peripheral devices 108, for example, the wireless communication system 146, the vehicle-mounted computer 148, the microphone 150, and the loudspeaker 152.

The computer system 112 may control the functions of the autonomous driving vehicle 100 based on inputs received from various subsystems (for example, the travel system 102, the sensor system 104, and the autonomous driving system 106) and the user interface 116. For example, the computer system 112 may use an input from the autonomous driving system 106 to control the steering system 132 to avoid the obstacles that are detected by the sensor system 104 and the obstacle avoidance system 144. In some embodiments, the computer system 112 may be operated to control many aspects of the autonomous driving vehicle 100 and the subsystems of the autonomous driving vehicle 100.

Optionally, one or more of the foregoing components may be installed separately from or associated with the autonomous driving vehicle 100. For example, the memory 114 may exist partially or completely separate from the autonomous driving vehicle 100. The foregoing components may be communicatively coupled together in a wired and/or wireless manner.

Optionally, the foregoing components are merely examples. In actual application, components in the foregoing modules may be added or deleted depending on an actual requirement. FIG. 4 should not be understood as any limitation on embodiments of this application. An autonomous driving vehicle traveling on a road, for example, the autonomous driving vehicle 100, may identify an object in the surrounding environment of the autonomous driving vehicle 100, to determine to adjust a current speed. The object may be another vehicle, a traffic control device, or another type of object. In some examples, each identified object may be considered independently and may be used to determine the speed to be adjusted by the autonomous driving vehicle, based on characteristics of each object, such as a current speed of the object, an acceleration of the object, and a spacing between the object and the vehicle.

Optionally, the autonomous driving vehicle 100 or a computing device (for example, the computer system 112, the computer vision system 140, or the memory 114 shown in FIG. 4) associated with the autonomous driving vehicle 100 may predict a behavior of the identified object based on the characteristics of the identified object and the status (for example, traffic, rain, or ice on a road) of the surrounding environment. Optionally, the identified objects depend on behaviors of each other. Therefore, all the identified objects may be considered together to predict a behavior of a single identified object. The autonomous driving vehicle 100 can adjust the speed of the autonomous driving vehicle 100 based on the predicted behavior of the identified object. In other words, the autonomous driving vehicle 100 can determine, based on the predicted behavior of the object, that the vehicle needs to be adjusted to a specific stable state (for example, an accelerated, decelerated, or stop state). In this process, another factor may also be considered to determine the speed of the autonomous driving vehicle 100, for example, a horizontal location of the autonomous driving vehicle 100 on a road on which the autonomous driving vehicle 100 travels, a curvature of the road, and proximity between a static object and a dynamic object. In addition to providing an instruction for adjusting the speed of the autonomous driving vehicle, the computing device may provide an instruction for modifying a steering angle of the autonomous driving vehicle 100, so that the autonomous driving vehicle 100 follows a given track and/or maintains safe transverse and longitudinal distances from an object (for example, a car in an adjacent lane on the road) near the autonomous driving vehicle 100.

The autonomous driving vehicle 100 may be a car, a truck, a motorcycle, a bus, a boat, an airplane, a helicopter, a lawn mower, a recreational vehicle, a playground vehicle, a construction device, a trolley, a golf cart, a train, a handcart, or the like. This is not specifically limited in this embodiment of this application.

Figure 5:
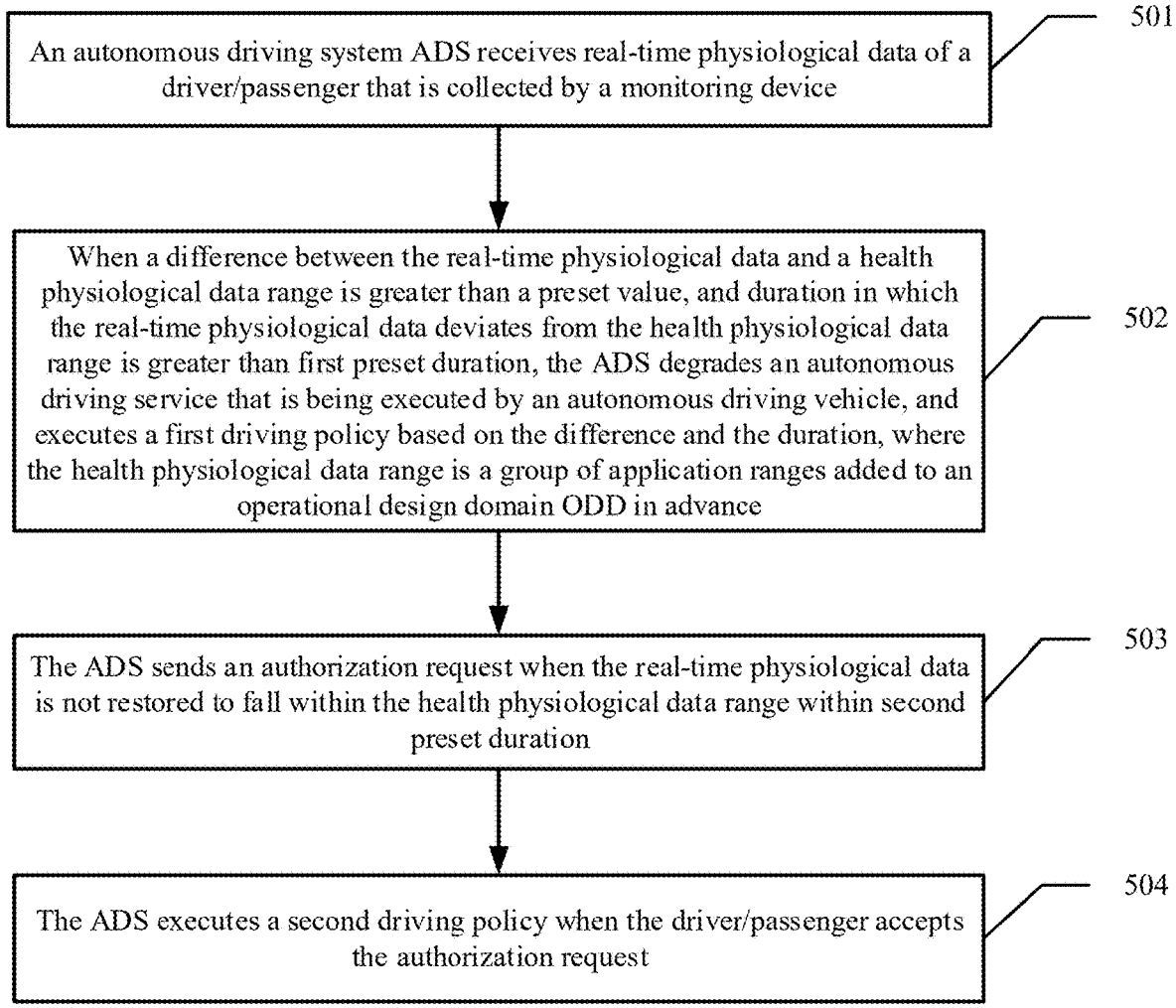
FIG. 5 is a schematic flowchart of an autonomous driving method according to an embodiment of this application.

Based on the autonomous driving vehicle described in the embodiment corresponding to FIG. 4, an embodiment of this application provides an autonomous driving method. FIG. 5 is a schematic flowchart of an autonomous driving method according to an embodiment of this application. The method may include the following steps.

501: An autonomous driving system ADS receives real-time physiological data of a driver/passenger that is collected by a monitoring device.

First, the driver/passenger in the autonomous driving vehicle in which the ADS is deployed wears the monitoring device (for example, a smart watch, a smart band, or a smart cardiotachometer, or another wearable device). The monitoring device may collect the real-time physiological data of the driver/passenger in real time, for example, may collect a heart rate, blood pressure, blood oxygen, a body temperature, a premature heartbeat, atrial fibrillation, and other real-time physiological data of the driver/passenger, and then send these pieces of collected real-time physiological data to the ADS by using a communication protocol (for example, Bluetooth or Wi-Fi).

It should be noted that in this embodiment of this application, the driver/passenger is essentially a person in a driving seat of the autonomous driving vehicle. When an autonomous driving level is L3 or a lower autonomous driving level, the driver/passenger may also be referred to as a driver in this case, and in some driving tasks, has a vehicle control right to control the autonomous driving vehicle. However, when an autonomous driving level is L4 or L5, the person in the driving seat of the autonomous driving vehicle does not have a vehicle control right to control the autonomous driving vehicle. In this case, the person cannot be referred to as a driver and is usually referred to as a driver/passenger. Therefore, the driver/passenger is a driver at the level L3 or below and is a driver/passenger at the level L4 or the level L5 in this embodiment of this application, and is collectively referred to as a driver/passenger in embodiments of this application.

502: When a difference between the real-time physiological data and a health physiological data range is greater than a preset value, and a duration in which the real-time physiological data deviates from the health physiological data range is greater than a first preset duration, the ADS degrades an autonomous driving service that is being executed by the autonomous driving vehicle, and executes a first driving policy based on the difference and the duration, where the health physiological data range is an applicable range added to an operational design domain ODD in advance.

After receiving the real-time physiological data of the driver/passenger that is sent by the monitoring device, the ADS determines whether the real-time physiological data deviates from the health physiological data range. When determining that the difference between the received real-time physiological data and the health physiological data range is greater than the preset value, the ADS further determines whether duration in which the real-time physiological data deviates from the health physiological data range is greater than the first preset duration. When determining that the duration in which the real-time physiological data deviates from the health physiological data range is greater than the first preset duration, the ADS performs degradation processing on the autonomous driving service that is being executed by the autonomous driving vehicle, and executes the first driving policy based on specific values of the difference and the duration.

It should be noted that the health physiological data range is the applicable range added to the ODD in advance. As shown in FIG. 2, an additional applicable range is used to indicate a health indicator of the driver/passenger, that is, the health physiological data range, for example, a normal heart rate range and a normal blood pressure range, is added to the ODD defined in the autonomous driving classification standard J3016TM. The ODD is deployed on the ADS. This can avoid a vehicle risk caused because a vehicle takeover person actually has no takeover capability in a specific time period due to a physical health problem. The newly added health physiological data range may be added to an ODD at each autonomous driving level, and in particular, needs to be added to ODDs at levels L3 to L5. Specifically, in an autonomous driving service related to the autonomous driving level L3, the ODD is integrated with the health indicator of the driver/passenger (a driver/passenger at the level L3 is a driver), that is, considers a driver takeover capability. In autonomous driving services related to the autonomous driving levels L4 and L5, the driver/passenger has no takeover obligation or approach, and corresponding ODDs also need to be integrated with the health indicator of the driver/passenger to guide the ADS to execute a subsequent risk mitigation strategy.

For case of understanding, the following describes step 502 by using an example in which the real-time physiological data collected by the monitoring device is a real-time heart rate and the health physiological data range is a health heart rate range. It is assumed that the health heart rate range is from 60 times per minute to 100 times per minute. If the real-time heart rate of the driver/passenger at a moment that is collected by the monitoring device ranges from 120 times per minute to 160 times per minute, which is beyond the health heart rate range, the ADS is triggered to start timing. It is assumed that the first preset duration is three minutes. After three minutes, the real-time heart rate collected by the monitoring device within the three minutes still ranges from 120 times per minute to 160 times per minute. To be specific, duration of the abnormal real-time heart rate is three minutes, and a difference between the real-time heart rate and the health heart rate range is from 20 times per minute to 60 times per minute, which is greater than a preset value (it is assumed that the preset value is 20 times per minute). Then, it indicates that there is a high probability that a health status of the driver/passenger is suddenly undesirable. In this case, the ADS degrades a "high-speed car-following driving" service that is being executed by the autonomous driving vehicle (it is assumed that the autonomous driving service being executed is the "high-speed car-following driving" service). For example, an original speed 100 kilometers/hour (unit: km/h) is slowly decreased to 70 km/h, and the first driving policy is executed based on the difference and the duration. For example, the first driving policy may be traveling on a roadside and turning on a hazard warning signal light for warning.

Because autonomous driving levels of the autonomous driving vehicle are specifically classified into L0 to L5, and different autonomous driving levels are corresponding to different ODDs, first driving policies at the levels L3, L4, and L5 are mainly considered in this embodiment of this application. The following separately provides descriptions.
(1) First Driving Policy when an Autonomous Driving Level is L3

If the autonomous driving level is the level L3, the driver/passenger is the driver in the driving seat of the autonomous driving vehicle. First, when the difference between the real-time physiological data and the health physiological data range is greater than the preset value, and the duration in which the real-time physiological data deviates from the health physiological data range is greater than the first preset duration, it indicates that there is a high probability that the health status of the driver/passenger is undesirable in this case. The ADS makes the ADS invariably occupy the control right of the autonomous driving vehicle, that is, the vehicle control right cannot be handed over to the driver/passenger. Then, the ADS further determines a health level of the driver/passenger based on the deviation difference and the deviation duration, and executes the corresponding first driving policy based on the health level. For example, when the ADS determines that the health level is a mild abnormality, in addition to making the ADS invariably occupy the control right of the autonomous driving vehicle, the first driving policy may be further any one or more of: controlling, by the ADS, the autonomous driving vehicle to decrease a speed to be lower than a preset speed (for example, lower than 60 km/h), travel on a roadside, and turn on a hazard warning signal light. When the ADS determines that the health level is a severe abnormality, in addition to making the ADS invariably occupy the control right of the autonomous driving vehicle, the first driving policy may be further any one or more of: controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and unlock a central door lock.

It should be noted that in this embodiment of this application, when the health status of the driver/passenger is undesirable, health levels are classified into a mild abnormality and a severe abnormality (if the real-time physiological data is within the health physiological data range, the health level is a normal level). For case of understanding, the following uses an example in which the real-time physiological data is a real-time heart rate to illustrate a manner of classifying the health levels of the driver/passenger. In this embodiment of this application, it is assumed that the health heart rate range is from 60 times per minute to 100 times per minute.

a. The health level is a normal level: The real-time heart rate of the driver/passenger ranges from 60 times per minute to 100 times per minute. In this case, the health level of the driver/passenger is a normal level, and may also be referred to as a health level 1, indicating that the health status of the driver/passenger is desirable.

b. The health level is a mild abnormality: The real-time heart rate of the driver/passenger ranges from 40 times per minute to 60 times per minute and lasts for three minutes, or the real-time heart rate of the driver/passenger ranges from 100 times per minute to 160 times per minute and lasts for three minutes. In this case, the health level of the driver/passenger is a mild abnormality, and may also be referred to as a health level 2, indicating that the driver/passenger has a mild health problem and the driver/passenger is slightly uncomfortable.

c. The health level is a severe abnormality: The real-time heart rate of the driver/passenger is less than 40 times per minute and lasts for five minutes, or the real-time heart rate of the driver/passenger is greater than 160 times per minute and lasts for five minutes. In this case, the health level of the driver/passenger is a severe abnormality, and may also be referred to as a health level 3, indicating that the driver/ passenger has a severe health problem and the driver/passenger is seriously uncomfortable.

It should be noted that the health heart rate range may be preset based on big data statistics, for example, may be set to 65 times per minute to 105 times per minute. This is not specifically limited herein. A difference and duration for determining a specific health level based on the real-time heart rate may also be preset. For example, a health level when the real-time heart rate of the driver/passenger ranges from 30 times per minute to 65 times per minute and lasts for four minutes or when the real-time heart rate of the driver/passenger ranges from 105 times per minute to 165 times per minute and lasts for three minutes may be set to a mild abnormality. This is not specifically limited herein.

It should also be noted that in some implementations of this application, takeover capability levels of taking over the vehicle control right by the driver/passenger may be correspondingly obtained based on the health level of the driver/passenger. The takeover capability levels are separately described as follows:

a. Takeover capability level 1: A corresponding health level is a normal level (or the health level 1). The autonomous driving service is not affected, and the driver/passenger can take over the vehicle control right at any time.

b. Takeover capability level 2: A corresponding health level is a mild abnormality (or the health level 2). The ADS controls the autonomous driving vehicle to degrade the autonomous driving service, that is, to decrease the speed to be not greater than 60 km/h, travel on a roadside, and turn on a hazard warning signal light. The vehicle control right cannot be handed over to the driver/passenger.

c. Takeover capability level 3: A corresponding health level is a severe abnormality (or the health level 3). The ADS controls the autonomous driving vehicle to continuously degrade the autonomous driving service, slowly decrease the speed to 0 and then exit, stop on a roadside, turn on a hazard warning signal light, run at an idle speed, turn on a ventilation/external circulation of the vehicle, set an in-vehicle target temperature to 22° C., turn on an air conditioner, unlock a central door lock, use an in-vehicle communication device (for example, a T-box) to call for help, and periodically send positioning information.

It should also be noted that the foregoing describes only three classified health levels: normal, a mild abnormality, and a severe abnormality, which are respectively corresponding to the level 1, the level 2, and the level 3. In some implementations of this application, more or fewer health levels may be set depending on an actual application scenario. For example, the health levels may be classified into only a normal level and an abnormality level, that is, are corresponding to two levels. Alternatively, the health levels may be classified into a normal level, a mild abnormality, a moderate abnormality, and a severe abnormality, that is, are corresponding to four levels. How to classify the health levels is not specifically limited herein. Only a mild abnormality and a severe abnormality are used as an example for illustration in embodiments of this application, to describe different first driving policies that may be used based on different health levels in embodiments of this application. This is more pertinent to specific cases.

Similarly, the foregoing describes only three classified takeover capability levels: the level 1, the level 2, and the level 3. In some implementations of this application, more or fewer takeover capability levels may be set depending on an actual application scenario. How to classify the takeover capability levels is not specifically limited herein.

It should also be noted that the foregoing merely uses an example in which the real-time physiological data is a real-time heart rate to illustrate a manner of classifying the health levels of the driver/passenger. In some implementations of this application, the real-time physiological data collected by the monitoring device may be alternatively real-time physiological data of the driver/passenger, for example, a heart rate, blood pressure, blood oxygen, a body temperature, a premature heartbeat, and atrial fibrillation, provided that the physiological data can be collected by the monitoring device and can reflect the health status of the driver/passenger. This is not specifically limited herein.

The following uses an example in which the real-time physiological data is a real-time heart rate and the health levels of the driver/passenger are classified to describe health level classification of the driver/passenger and corresponding first driving policies. Details may be described in Table 2. The health physiological data range in the ODD is correspondingly the health heart rate range. In this embodiment of this application, it is assumed that the health heart rate range is from 60 times per minute to 100 times per minute. If a health level being a normal level is corresponding to the level 1, it indicates that a driver/passenger takeover capability is the level 1, and the autonomous driving service that is being executed by the autonomous driving vehicle is not affected. If a health level being a mild abnormality is corresponding to the level 2, the ADS controls the autonomous driving service that is being executed by the autonomous driving vehicle to degrade, and controls the autonomous driving vehicle to perform any one or more of the following: decreasing a speed to be lower than a preset speed, traveling on a roadside, and turning on a hazard warning signal light. If a health level being a severe abnormality is corresponding to the level 3, the ADS controls the autonomous driving service that is being executed by the autonomous driving vehicle to be continuously degraded, and controls the autonomous driving vehicle to perform any one or more of the following: slowly decreasing the speed to zero, stopping on a roadside, turning on a hazard warning signal light, running at an idle speed, turning on an external circulation of the vehicle, turning on an internal circulation of the vehicle, setting an in-vehicle target temperature, and unlocking a central door lock.

TABLE 2

Health level classification of a driver/passenger and corresponding first driving policies in the case of L3

| Real-time physiological data of a driver/passenger (using a real-time heart rate as an example) | Health level classification | First driving policy |
| --- | --- | --- |
| A real-time heart rate ranges from 60 times per minute to 100 times per minute. | Level 1: healthy | An autonomous driving service is running normally. A vehicle control right can be handed over to a driver. |

TABLE 2-continued

Health level classification of a driver/passenger and corresponding first driving policies in the case of L3

| Real-time physiological data of a driver/passenger (using a real-time heart rate as an example) | Health level classification | First driving policy |
|---|---|---|
| A real-time heart rate ranges from 40 times per minute to 60 times per minute and lasts for three minutes, or a real-time heart rate ranges from 100 times per minute to 160 times per minute and lasts for three minutes. | Level 2: mildly abnormal | An autonomous driving service is degraded. A vehicle control right cannot be handed over to a driver. An ADS controls an autonomous driving vehicle to perform any one or more of the following: decreasing a speed to be lower than a preset speed, traveling on a roadside, and turning on a hazard warning signal light. |
| A real-time heart rate is less than 40 times per minute and lasts for five minutes, or a real-time heart rate is greater than 160 times per minute and lasts for five minutes. | Level 3: severely abnormal | An autonomous driving service is continuously degraded. A vehicle control right cannot be handed over to a driver. An ADS controls an autonomous driving vehicle to perform any one or more of the following: slowly decreasing a speed to zero, stopping on a roadside, turning on a hazard warning signal light, running at an idle speed, turning on an external circulation of the vehicle, turning on an internal circulation of the vehicle, setting an in-vehicle target temperature, and unlocking a central door lock. |

If the autonomous driving level is L3, in this embodiment of this application, the health level is determined based on the difference between the real-time physiological data and the health physiological data range and the deviation duration, and different first driving policies are used based on different health levels. This is more pertinent to specific cases. Moreover, in this embodiment of this application, the driver/passenger has a right to take over the vehicle control right only when the health level of the driver/passenger is a normal level; otherwise, the vehicle control right cannot be handed over to the driver/passenger, and the ADS executes the first driving policy. This avoids a vehicle risk and a personal safety problem caused because the driver/passenger actually has no takeover capability in a specific time period due to a physical health problem.

(2) First Driving Policy when an Autonomous Driving Level is L4 or L5

If the autonomous driving level is the level L4 or the level L5, the person in the driving seat of the autonomous driving vehicle does not have a vehicle control right to control the autonomous driving vehicle. In this case, the person cannot be referred to as a driver and is usually referred to as a driver/passenger. First, when the difference between the real-time physiological data and the health physiological data range is greater than the preset value, and the duration in which the real-time physiological data deviates from the health physiological data range is greater than the first preset duration, it indicates that there is a high probability that a health status of the driver/passenger is undesirable in this case. Then, the ADS further determines a health level of the driver/passenger based on the deviation difference and the deviation duration, and executes the corresponding first driving policy based on the health level. This is similar to the foregoing case in which the autonomous driving level is L3. For example, when the ADS determines that the health level is a mild abnormality, the first driving policy may be any one or more of: controlling, by the ADS, the autonomous driving vehicle to decrease a speed to be lower than a preset speed (for example, lower than 60 km/h), travel on a roadside, and turn on a hazard warning signal light. When the ADS determines that the health level is a severe abnormality, the first driving policy may be any one or more of: controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and unlock a central door lock.

It should be noted that, in this embodiment of this application, similar to the foregoing case in which the autonomous driving level is L3, when the health status of the driver/passenger is undesirable, health levels are classified into a mild abnormality and a severe abnormality (if the real-time physiological data is within the health physiological data range, the health level is a normal level). For details, refer to the foregoing case of L3. Details are not described herein again.

The following uses an example in which the real-time physiological data is a real-time heart rate and the health levels of the driver/passenger are classified to describe health level classification of the driver/passenger and corresponding first driving policies. Details may be described in Table 3. The health physiological data range in the ODD is correspondingly the health heart rate range. In this embodiment of this application, it is assumed that the health heart rate range is from 60 times per minute to 100 times per minute. If a health level being a normal level is corresponding to the level 1, the autonomous driving service that is being executed by the autonomous driving vehicle is not affected. If a health level being a mild abnormality is corresponding to the level 2, the ADS controls the autonomous driving service that is being executed by the autonomous driving vehicle to degrade, and controls the autonomous driving vehicle to perform any one or more of the following: decreasing a speed to be lower than a preset speed, traveling on a roadside, and turning on a hazard warning signal light. If a health level being a severe abnormality is corresponding to the level 3, the ADS controls the autonomous driving service that is being executed by the autonomous driving vehicle to be continuously degraded, and controls the autonomous driving vehicle to perform any one or more of the following: slowly decreasing the speed to zero, stopping on a roadside, turning on a hazard warning signal light, running at an idle speed, turning on an external circulation of the vehicle, turning on an internal circulation of the vehicle, setting an in-vehicle target temperature, and unlocking a central door lock. A difference between Table 3 and Table 2 lies in that the first driving policy in Table 3 does not involve a handover of the vehicle control right, because at the level L4 or the level L5, the driver/passenger has no obligation or approach to take over the vehicle.

within eight minutes), the ADS sends an authorization request to the driver/passenger. The authorization request may be communicated to the driver/passenger in a voice broadcast manner, or may be communicated to the driver/passenger in an interface display manner (with a premise that a display is deployed on the autonomous driving vehicle). This is not specifically limited herein. The authorization request is used to ask the driver/passenger whether a second driving policy needs to be executed.

504: The ADS executes the second driving policy when the driver/passenger accepts the authorization request.

After the driver/passenger receives the authorization request sent by the ADS, the ADS executes the second driving policy when the driver/passenger accepts the authorization request. The second driving policy may be any one or more of the following: stopping on a roadside, calling for a rescue, establishing a communication connection to a medical institution, planning a traveling path between the autonomous driving vehicle and the medical institution,

TABLE 3

Health level classification of a driver/passenger and corresponding first driving policies in the case of L4 or L5

| Real-time physiological data of a driver/passenger (using a real-time heart rate as an example) | Health level classification | First driving policy |
| --- | --- | --- |
| A real-time heart rate ranges from 60 times per minute to 100 times per minute. | Level 1: healthy | An autonomous driving service is running normally. |
| A real-time heart rate ranges from 40 times per minute to 60 times per minute and lasts for three minutes, or a real-time heart rate ranges from 100 times per minute to 160 times per minute and lasts for three minutes. | Level 2: mildly abnormal | An autonomous driving service is degraded. An ADS controls an autonomous driving vehicle to perform any one or more of the following: decreasing a speed to be lower than a preset speed, traveling on a roadside, and turning on a hazard warning signal light. |
| A real-time heart rate is less than 40 times per minute and lasts for five minutes, or a real-time heart rate is greater than 160 times per minute and lasts for five minutes. | Level 3: severely abnormal | An autonomous driving service is continuously degraded. An ADS controls an autonomous driving vehicle to perform any one or more of the following: slowly decreasing a speed to zero, stopping on a roadside, turning on a hazard warning signal light, running at an idle speed, turning on an external circulation of the vehicle, turning on an internal circulation of the vehicle, setting an in-vehicle target temperature, and unlocking a central door lock. |

If the autonomous driving level is L4 or L5, in this embodiment of this application, the health level is determined based on the difference between the real-time physiological data and the health physiological data range and the deviation duration, and different first driving policies are used based on different health levels. This is more pertinent to specific cases.

503: The ADS sends an authorization request when the real-time physiological data is not restored to fall within the health physiological data range within a second preset duration.

Regardless of a specific autonomous driving level, when the real-time physiological data collected by the monitoring device is not restored to fall within the health physiological data range within the second preset duration (for example, reserving a medical resource, and requesting to arrange an emergency medical treatment channel.

In the implementation of this application, the second driving policy is essentially an upgrade of an original risk mitigation strategy. For the original risk mitigation strategy, regardless of a specific autonomous driving level, when the ADS cannot perform a dynamic driving task or the driver/passenger cannot take over a dynamic driving task, a final objective of the risk mitigation strategy is "stopping the vehicle", that is, only vehicle safety in a narrow sense is considered. However, in embodiments of this application, for the second driving policy, in addition to considering stopping the vehicle, more efforts may be made in the vehicle in an actual situation, including but not limited to measures such as calling for help, organizing a rescue, requesting to arrange an emergency access, and reserving a medical resource, especially within "first aid platinum 10 minutes" when it is detected that the driver/passenger is uncomfortable. The "first aid platinum 10 minutes" are first 10 minutes from start time when the driver/passenger is sent to an emergency department or an emergency room of a related department of a hospital to time when a doctor performs emergency treatment, after an emergency event occurs, regardless of a specific procedure. Earlier 10 minutes lead to a higher value. This is of great meaning and significance in guiding doctors to establish a time-efficiency view in an emergency specialty.

It should be noted that in some implementations of this application, step 503 and step 504 may not be included.

It should also be noted that in some implementations of this application, if the driver/passenger does not accept the authorization request, it indicates that the driver/passenger considers that the driver/passenger can handle a sudden health accident well, for example, the driver/passenger has carried first-aid medicine. In this case, the ADS may execute the original risk mitigation strategy. For example, assuming that the real-time physiological data is a real-time heart rate, in a scenario related to a heart rate, even if the health level of the driver/passenger is an abnormality level, the driver/passenger is still conscious. The ADS needs to first query about intention of the driver/passenger before executing the second driving policy, for example, using an in-vehicle communication device (for example, a T-box) to call for help or call for an emergency medical resource, because if error reports are frequent, user experience is poor and the autonomous driving service that is being executed is frequently degraded. In this way, the intention of the driver/passenger is respected, and occasional indeterminate error reporting of the monitoring device can be avoided. In addition, time for discovering a health problem is advanced (because the driver/passenger may not perceive obvious discomfort if a mild abnormality occurs), so that advance detection and timely handling are implemented. In this way, user experience is desirable, and health of the driver/passenger is ensured. This reduces an occurrence rate of traffic accidents, and also brings huge social benefits.

It should also be noted that in some implementations of this application, regardless of a specific autonomous driving level, when the real-time physiological data collected by the monitoring device is restored to fall within the health physiological data range within the second preset duration (for example, within eight minutes), it indicates that the health status of the driver/passenger is temporarily restored. In this case, the ADS may control the autonomous driving vehicle to recover a degraded autonomous driving service. For example, it is assumed that the original autonomous driving service that is being executed by the autonomous driving vehicle is "high-speed car-following driving at a speed of 100 km/h", and the difference between the real-time physiological data and the health physiological data range exceeds the preset value for the first preset duration (for example, three minutes). Then, the ADS degrades the autonomous driving service to "high-speed car-following driving at a speed of 60 km/h", and continuously monitors subsequently collected real-time physiological data. If the monitored real-time physiological data is restored to fall within the health physiological data range within the second preset duration (for example, within eight minutes), the ADS restores the degraded "high-speed car-following driving at a speed of 60 km/h" autonomous driving service to the original "high-speed car-following driving at a speed of 100 km/h".

It should also be noted that in some implementations of this application, the ADS may further generate an event log based on the real-time physiological data, where the event log is used to record abnormal real-time physiological data and a series of subsequent operations of the ADS during a period when the real-time physiological data deviates from the health physiological data range; and periodically report the event log to a cloud server corresponding to the autonomous driving vehicle. This is convenient to distinguish responsibilities between the person and the vehicle. For case of understanding, the following uses an example for description. It is assumed that a time in which the real-time physiological data of the driver/passenger that is collected by the monitoring device deviates from the health physiological data range is from 10:00 to 10:10 on Sep. 6, 2020, and the health level is a mild abnormality. The ADS uses the first driving policy for the health level, and when the driver/passenger rejects the authorization request, the ADS controls the autonomous driving vehicle to execute the original risk mitigation strategy. In this case, an event log is generated in the corresponding time period from 10:00 to 10:10 on Sep. 6, 2020. The event log records real-time physiological data and a series of operations of the ADS that are corresponding to the time period. The series of operations are as follows: The first driving policy is used for the health level, and when the driver/passenger rejects the authorization request, the autonomous driving is controlled to execute the original risk mitigation strategy.

It should be noted that in this embodiment of this application, the autonomous driving levels are not distinguished between each other for the second driving policy. In other words, regardless of the level L3, the level L4, or the level L5, the second driving policy may be any one or more of the following: stopping on a roadside, calling for a rescue, establishing a communication connection to a medical institution, planning a traveling path between the autonomous driving vehicle and the medical institution, reserving a medical resource, and requesting to arrange an emergency medical treatment channel. However, in an actual application process, different second driving policies may be used for different autonomous driving levels. This is more pertinent to specific cases, and can improve user experience. The following separately provides descriptions.

(1) Second Driving Policy when an Autonomous Driving Level is L3

If the autonomous driving level is L3, the driver/passenger (actually the driver at the level L3) has greater discourse power in this case. Therefore, the ADS may query about the intention of the driver/passenger in advance in execution of each step of the second driving policy. For example, when the driver/passenger accepts the authorization request, if the health level of the driver/passenger is a mild abnormality, the ADS may plan a route between a medical institution closest to the ADS and the ADS, and re-send an authorization request "the route to the nearest medical institution has been planned, whether to go". If the driver/passenger agrees to go, the ADS may control the autonomous driving vehicle to go to the medical institution. For another example, when the driver/passenger accepts the authorization request, if the health level of the driver/passenger is a severe abnormality, the ADS may send an authorization request such as "whether to call for a rescue" or "whether to reserve a medical resource", plan a route between a medical institution closest to the ADS and the ADS, and send another authorization request "the route to the nearest medical institution has been planned, whether to go". If the driver/passenger agrees on both the authorization requests, the ADS may call for a rescue, and simultaneously control the autonomous driving vehicle to go to the medical institution.

For case of understanding, the following uses an example in which the real-time physiological data is a real-time heart rate and the health levels of the driver/passenger are classified to describe health level classification of the driver/passenger, and corresponding first driving policies, second driving policies, and event log reporting. Details may be described in Table 4. The health physiological data range in the ODD is correspondingly the health heart rate range. In this embodiment of this application, it is assumed that the health heart rate range is from 60 times per minute to 100 times per minute.

TABLE 4

Health level classification of a driver/passenger, and corresponding first/second driving policies and event log reporting in the case of L3

| Real-time physiological data of a driver/passenger (using a real-time heart rate as an example) | Health level classification | First driving policy | Second driving policy | Event log |
|---|---|---|---|---|
| A real-time heart rate ranges from 60 times per minute to 100 times per minute. | Level 1: healthy | An autonomous driving service is running normally. A vehicle control right can be handed over to a driver. | N/A | N/A |
| A real-time heart rate ranges from 40 times per minute to 60 times per minute and lasts for three minutes, or a real-time heart rate ranges from 100 times per minute to 160 times per minute and lasts for three minutes. | Level 2: mildly abnormal | An autonomous driving service is degraded. A vehicle control right cannot be handed over to a driver. An ADS controls an autonomous driving vehicle to perform any one or more of the following: decreasing a speed to be lower than a preset speed, traveling on a roadside, and turning on a hazard warning signal light. | Query whether the driver/passenger feels well. After consent of the driver/passenger is obtained, execute the second driving policy, including but not limited to any one or more of the following: calling for a rescue, establishing a communication connection to a medical institution, planning a traveling path between the autonomous driving vehicle and the medical institution, reserving a medical resource, and requesting to arrange an emergency medical treatment channel. | Record abnormal real-time physiological data and a series of subsequent operations of the ADS during a period when real-time physiological data deviates from a health physiological data range; and periodically report the event log to a cloud server corresponding to the autonomous driving vehicle. |
| A real-time heart rate is less than 40 times per minute and lasts for five minutes, or a real-time heart rate is greater than 160 times per minute and lasts for five minutes. | Level 3: severely abnormal | An autonomous driving service is continuously degraded. A vehicle control right cannot be handed over to a driver. An ADS controls an autonomous driving vehicle to perform any one or more of the following: slowly decreasing a speed to zero, stopping on a roadside, turning on a hazard warning signal light, running at an idle speed, turning on an external circulation of the vehicle, turning on an internal circulation of the vehicle, setting an in-vehicle target temperature, and unlocking a central door lock. | | |

It should be noted that the foregoing second driving policy when the autonomous driving level is L3 is merely an example. In an actual application scenario, a specific implementation of the second driving policy may be set depending on a requirement. This is not limited herein.

(2) Second Driving Policy when an Autonomous Driving Level is L4 or L5

If the autonomous driving levels are L4 and L5, the driver/passenger has no obligation or approach to take over the vehicle in this case. Therefore, after the ADS sends an authorization request when the real-time physiological data is not restored to fall within the health physiological data range within the second preset duration, if the driver/passenger accepts the authorization request, the ADS directly executes the second driving policy, and subsequently does not query about the intention of the driver/passenger. For example, it is assumed that the specified second driving policy is "planning a traveling path between the autonomous driving vehicle and a nearest medical institution and going, and requesting the nearest medical institution to arrange an emergency medical treatment channel". Then, when the driver/passenger accepts the authorization request, the ADS directly controls the autonomous driving vehicle to plan the traveling path between the autonomous driving vehicle and the nearest medical institution and go, and requests, by using a communication device on the autonomous driving vehicle, the nearest medical institution to arrange an emergency medical treatment channel. In some implementations of this application, the ADS may broadcast an execution status of the second driving policy to the driver/passenger in real time.

Likewise, for ease of understanding, the following uses an example in which the real-time physiological data is a real-time heart rate and the health levels of the driver/passenger are classified to describe health level classification of the driver/passenger, and corresponding first driving policies, second driving policies, and event log reporting. Details may be described in Table 5. The health physiological data range in the ODD is correspondingly the health heart rate range. In this embodiment of this application, it is assumed that the health heart rate range is from 60 times per minute to 100 times per minute. A difference between Table 5 and Table 4 lies in that the first driving policy in Table 5 does not involve a handover of the vehicle control right, because at the level L4 or the level L5, the driver/passenger has no obligation or approach to take over the vehicle.

TABLE 5

Health level classification of a driver/passenger, and corresponding first/second driving policies and event log reporting in the case of L4 or L5

| Real-time physiological data of a driver/passenger (using a real-time heart rate as an example) | Health level classification | First driving policy | Second driving policy | Event log |
|---|---|---|---|---|
| A real-time heart rate ranges from 60 times per minute to 100 times per minute. | Level 1: healthy | An autonomous driving service is running normally. | N/A | N/A |
| A real-time heart rate ranges from 40 times per minute to 60 times per minute and lasts for three minutes, or a real-time heart rate ranges from 100 times per minute to 160 times per minute and lasts for three minutes. | Level 2: mildly abnormal | An autonomous driving service is degraded. An ADS controls an autonomous driving vehicle to perform any one or more of the following: decreasing a speed to be lower than a preset speed, traveling on a roadside, and turning on a hazard warning signal light. | Query whether the driver/passenger feels well. After consent of the driver/passenger is obtained, execute the second driving policy, including but not limited to any one or more of the following: calling for a rescue, | Record abnormal real-time physiological data and a series of subsequent operations of the ADS during a period when real-time physiological data deviates from a health physiological data range; and periodically |
| A real-time heart rate is less than 40 times per minute and lasts for five minutes, or a real-time heart rate is greater than 160 times per minute and lasts for five minutes. | Level 3: severely abnormal | An autonomous driving service is continuously degraded. An ADS controls an autonomous driving vehicle to perform any one or more of the following: slowly decreasing a speed to zero, stopping on a roadside, turning on a hazard warning signal light, running at an idle speed, turning on an | establishing a communication connection to a medical institution, planning a traveling path between the autonomous driving vehicle and the medical institution, reserving a medical resource, and requesting to | report the event log to a cloud server corresponding to the autonomous driving vehicle. |

TABLE 5-continued

Health level classification of a driver/passenger, and corresponding first/second driving policies and event log reporting in the case of L4 or L5

| Real-time physiological data of a driver/passenger (using a real-time heart rate as an example) | Health level classification | First driving policy | Second driving policy | Event log |
|---|---|---|---|---|
| | | external circulation of the vehicle, turning on an internal circulation of the vehicle, setting an in-vehicle target temperature, and unlocking a central door lock. | arrange an emergency medical treatment channel. | |

It should be noted that, similarly, the foregoing second driving policy when the autonomous driving level is the level L4 or the level L5 is merely an example. In an actual application scenario, a specific implementation of the second driving policy may be set depending on a requirement. This is not limited herein.

For ease of understanding, the following uses two specific examples to separately describe autonomous driving methods provided in embodiments of this application when the autonomous driving level is the level L3 and when the autonomous driving level is the level L4 or the level L5. An example in which the real-time physiological data is a heart rate and the health physiological data range is the health heart rate range from 60 times per minute to 100 times per minute is used for illustration.

A. An Example of an Autonomous Driving Method in the Case of the Level L3

First, health levels of a driver/passenger are defined (the driver/passenger is actually a driver in the case of L3). For details, refer to Table 2. Details are not described herein again. Second, an autonomous driving vehicle needs to have several prerequisites: (1) The driver/passenger wears a monitoring device (for example, a smart watch) that collects real-time physiological data. The monitoring device may be configured to collect a heart rate, blood pressure, blood oxygen, a body temperature, a premature heartbeat, atrial fibrillation, and the like of the driver/passenger, and may send these pieces of collected real-time physiological data to an ADS by using a communication protocol (for example, Bluetooth or Wi-Fi). (2) The autonomous driving vehicle has a specific human-computer interaction capability (for example, a voice answer function). (3) The autonomous driving vehicle has a function of performing basic voice communication with an external world.

Figure 6A:
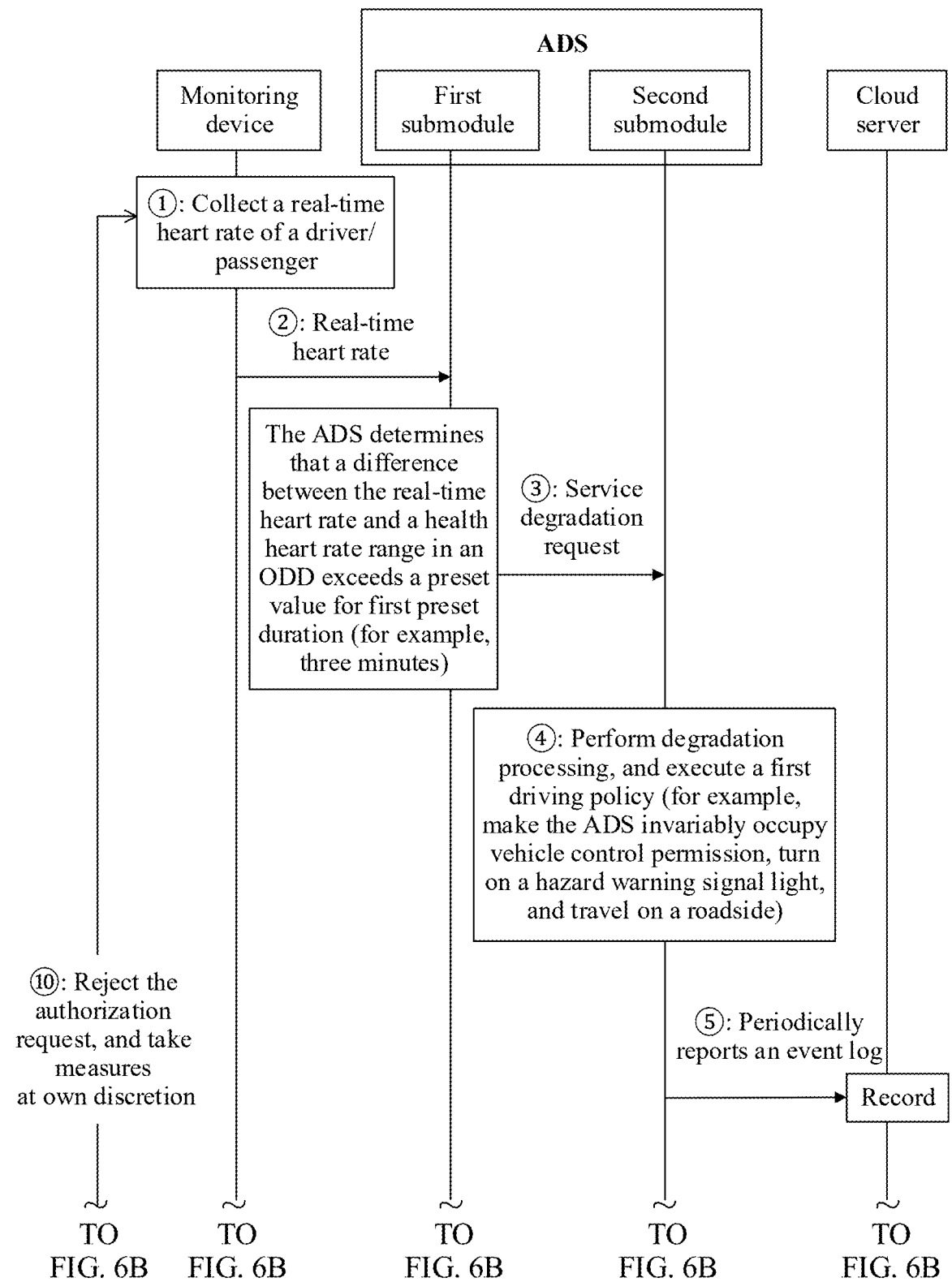
FIG. 6A and FIG. 6B are a schematic diagram of an example of an autonomous driving method according to an embodiment of this application.
Figure 6B:
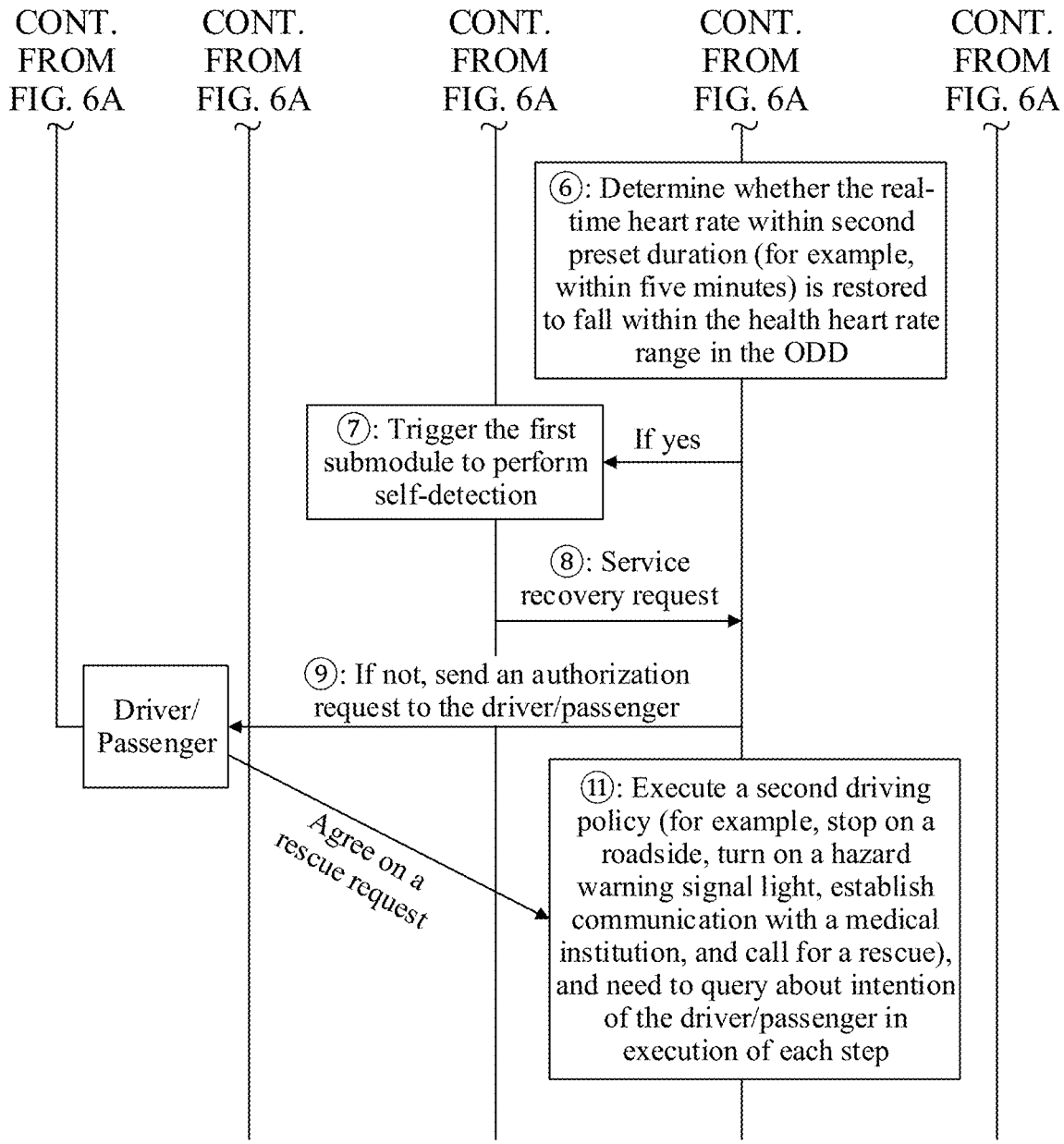

FIG. 6A and FIG. 6B show an example of an autonomous driving method in the case of a level L3 according to an embodiment of this application. The example may include the following steps.

Step 1: A monitoring device collects a real-time heart rate of a driver/passenger.

Step 2: The monitoring device sends the collected real-time heart rate to a first submodule of an ADS, where the first submodule is configured to determine whether the real-time heart rate deviates from a health heart rate range in an ODD.

Step 3: When the ADS determines that a difference between the real-time heart rate and the health heart rate range in the ODD exceeds a preset value for first preset duration (for example, three minutes), the first submodule of the ADS sends a service degradation request to a second submodule of the ADS, where the service degradation request is used to indicate the second submodule of the ADS to perform degradation processing on an autonomous driving service that is being executed by an autonomous driving vehicle, for example, decrease a speed of the vehicle.

Step 4: The second submodule of the ADS performs, based on the service degradation request, degradation processing on the autonomous driving service that is being executed by the autonomous driving vehicle, and the second submodule of the ADS controls the autonomous driving vehicle to execute a first driving policy, for example, make the ADS invariably occupy a vehicle control right, turn on a hazard warning signal light, and travel on a roadside.

Step 5: The second submodule of the ADS periodically reports an event log to a cloud server, so that the cloud server corresponding to the ADS needs to record operations, for example, performing service degradation by the ADS and executing the first driving policy by the ADS. This is convenient to subsequently distinguish responsibilities between the person and the vehicle.

Step 6: The second submodule of the ADS further determines whether the real-time heart rate collected within a second preset duration (for example, within five minutes) is restored to fall within the health heart rate range in the ODD.

Step 7: If the collected real-time heart rate is restored to fall within the health heart rate range in the ODD, trigger the first submodule of the ADS to perform status self-detection.

Step 8: After completing self-detection, the first submodule of the ADS sends a service recovery request to the second submodule of the ADS, where the service recovery request is used to indicate the second submodule of the ADS to recover a degraded autonomous driving service, for example, perform acceleration to reach an original traveling speed.

Step 9: If the collected real-time heart rate is not restored to fall within the health heart rate range in the ODD, send an authorization request to the driver/passenger by using an in-vehicle communication device, where the authorization request is used to query about a second driving policy, for example, query whether a rescue or nearby medical treatment is needed.

Step 10: If the driver/passenger rejects the authorization request, it indicates that the driver/passenger considers that a health status of the driver/passenger can be restored (for example, the driver/passenger has carried first-aid medicine), and the driver/passenger may take measures at own discretion in this case.

Step 11: If the driver/passenger agrees on the authorization request, the second submodule of the ADS may execute the second driving policy, and needs to query about intention of the driver/passenger in execution of each step.

It can be learned from the foregoing steps that the example of the autonomous driving method provided in this embodiment of this application has the following advantages:

(1) If the autonomous driving level is L3, health of the driver/passenger is considered. The driver/passenger can take over the vehicle control right only when a health level of the driver/passenger is a normal level; otherwise, the autonomous driving service is degraded according to the foregoing step logic, and the autonomous driving vehicle is controlled to execute the first driving policy and the second driving policy.

(2) A requirement of "first aid platinum 10 minutes" is fully considered. In a scenario related to a heart rate, even if the health level of the driver/passenger is an abnormality level, the driver/passenger is still conscious. The ADS needs to first query about the intention of the driver/passenger before executing the second driving policy, for example, using an in-vehicle communication device (for example, a T-box) to call for help or call for an emergency medical resource, because if error reports are frequent, user experience is poor and the autonomous driving service that is being executed is frequently degraded. In this way, the intention of the driver/passenger is respected, and occasional indeterminate error reporting of the monitoring device can be avoided. In addition, time for discovering a health problem is advanced (because the driver/passenger may not perceive obvious discomfort if a mild abnormality occurs), so that advance detection and timely handling are implemented. In this way, user experience is desirable, and health of the driver/passenger is ensured. This reduces an occurrence rate of traffic accidents, and also brings huge social benefits.

(3) Continuity of the autonomous driving service is ensured. If a physical status of the driver/passenger is recovered (considering that the driver/passenger has carried first-aid medicine to be taken), a takeover capability level gradually decreases (for example, decreases from a level 3 to a level 2). In addition, if the ODD of the autonomous driving service has no abnormal indicator in addition to a normal takeover capability indicator of the driver/passenger, the ADS controls the autonomous driving service to be recovered when the real-time physiological data of the driver/passenger is restored to fall within the health physiological data range.

(4) Responsibilities between the person and the vehicle are clear. The ADS may record, as the event log, all health-related data and operations during a period when the real-time physiological data is abnormal, and periodically (for example, every five minutes) report the event log to the cloud end corresponding to the autonomous driving vehicle for backup.

B. An Example of an Autonomous Driving Method in the Case of the Level L4 or the Level L5

Similarly, first, health levels of a driver/passenger also need to be defined. For details, refer to Table 3. Details are not described herein again. Second, an autonomous driving vehicle also needs to have several prerequisites: (1) The driver/passenger wears a monitoring device (for example, a smart watch) that collects real-time physiological data. The monitoring device may be configured to collect a heart rate, blood pressure, blood oxygen, a body temperature, a premature heartbeat, atrial fibrillation, and the like of the driver/passenger, and may send these pieces of collected real-time physiological data to an ADS by using a communication protocol (for example, Bluetooth or Wi-Fi). (2) The autonomous driving vehicle has a specific human-computer interaction capability (for example, a voice answer function). (3) The autonomous driving vehicle has a function of performing basic voice communication with an external world.

Figure 7A:
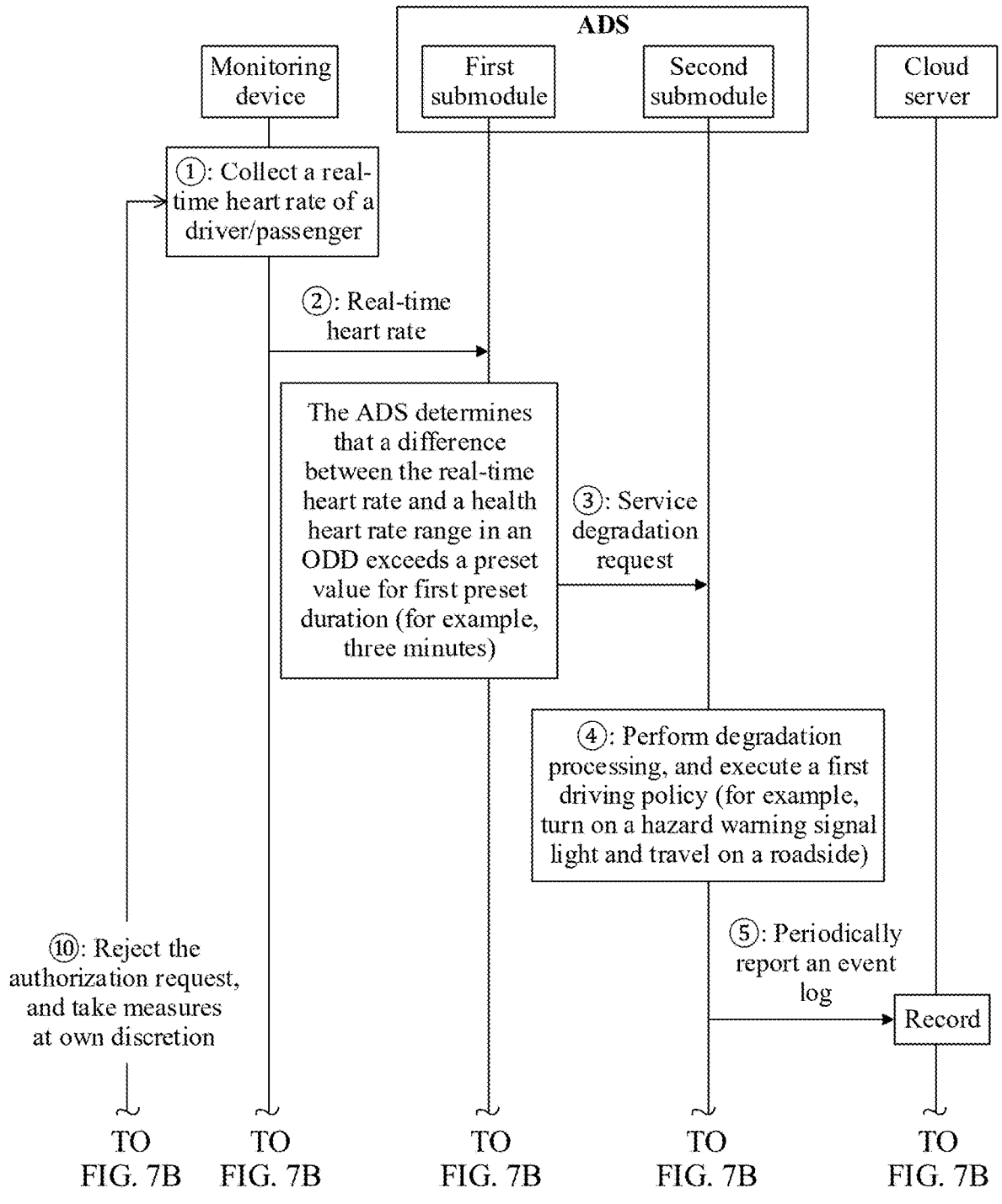
FIG. 7A and FIG. 7B are a schematic diagram of another example of an autonomous driving method according to an embodiment of this application.
Figure 7B:
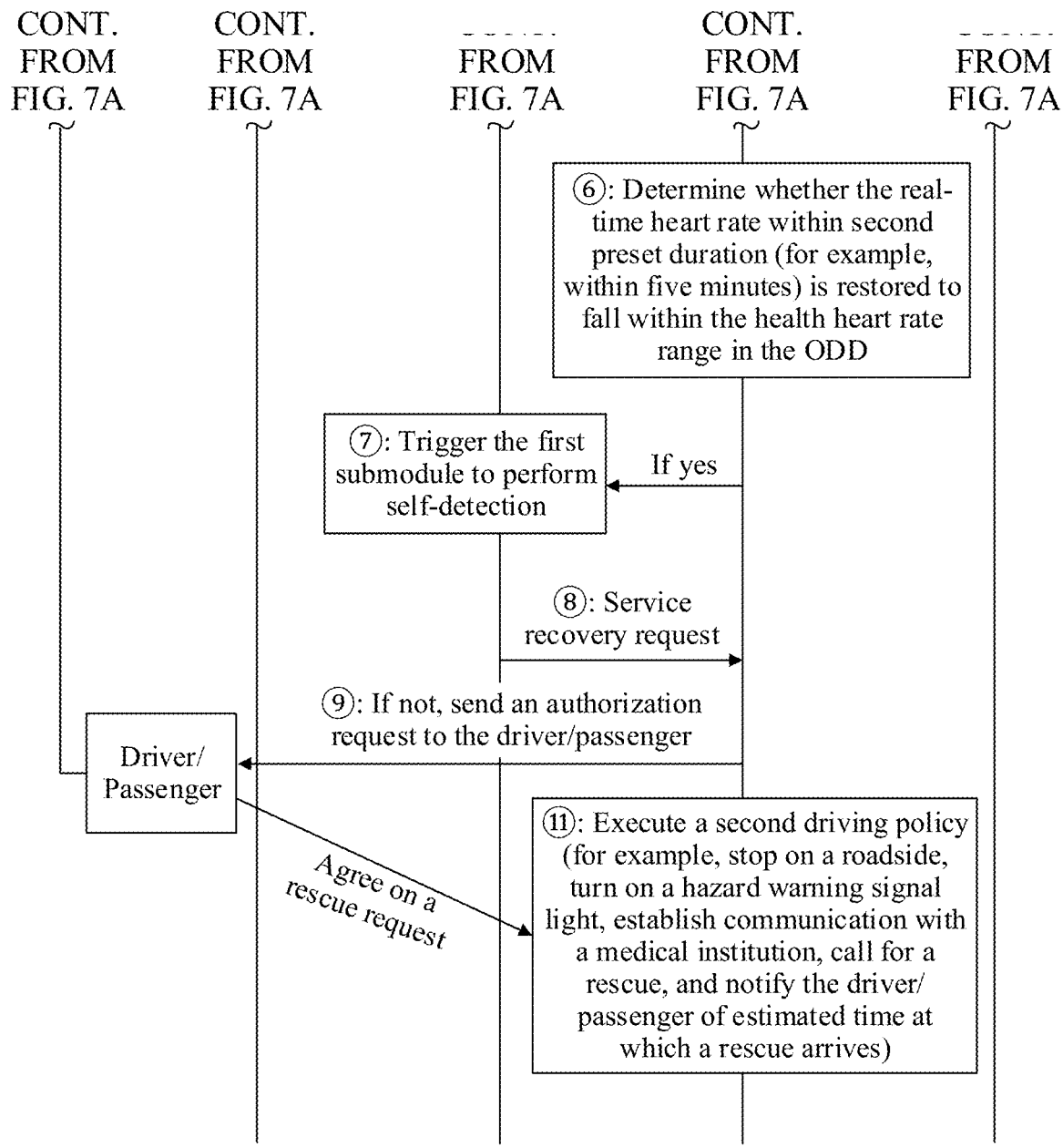

For details, refer to FIG. 7A and FIG. 7B. FIG. 7A and FIG. 7B show an example of an autonomous driving method in the case of a level L4 or a level L5 according to an embodiment of this application. The example may include the following steps.

Step 1: A monitoring device collects a real-time heart rate of a driver/passenger.

Step 2: The monitoring device sends the collected real-time heart rate to a first submodule of an ADS, where the first submodule is configured to determine whether the real-time heart rate deviates from a health heart rate range in an ODD.

Step 3: When the ADS determines that a difference between the real-time heart rate and the health heart rate range in the ODD exceeds a preset value for first preset duration (for example, three minutes), the first submodule of the ADS sends a service degradation request to a second submodule of the ADS, where the service degradation request is used to indicate the second submodule of the ADS to perform degradation processing on an autonomous driving service that is being executed by an autonomous driving vehicle, for example, decrease a speed of the vehicle.

Step 4: The second submodule of the ADS performs, based on the service degradation request, degradation processing on the autonomous driving service that is being executed by the autonomous driving vehicle, and the second submodule of the ADS controls the autonomous driving vehicle to execute a first driving policy, for example, turn on a hazard warning signal light and travel on a roadside.

Step 5: The second submodule of the ADS periodically reports an event log to a cloud server, so that the cloud server corresponding to the ADS needs to record operations, for example, performing service degradation by the ADS and executing the first driving policy by the ADS. This is convenient to subsequently distinguish responsibilities between the person and the vehicle.

Step 6: The second submodule of the ADS further determines whether the real-time heart rate collected within a second preset duration (for example, within five minutes) is restored to fall within the health heart rate range in the ODD.

Step 7: If the collected real-time heart rate is restored to fall within the health heart rate range in the ODD, trigger the first submodule of the ADS to perform status self-detection.

Step 8: After completing self-detection, the first submodule of the ADS sends a service recovery request to the second submodule of the ADS, where the service recovery request is used to indicate the second submodule of the ADS to recover a degraded autonomous driving service, for example, perform acceleration to reach an original traveling speed.

Step 9: If the collected real-time heart rate is not restored to fall within the health heart rate range in the ODD, send an authorization request to the driver/passenger by using an in-vehicle communication device, where the authorization request is used to query about a second driving policy, for example, query whether a rescue or nearby medical treatment is needed.

Step 10: If the driver/passenger rejects the authorization request, it indicates that the driver/passenger considers that a health status of the driver/passenger can be restored (for example, the driver/passenger has carried first-aid medicine), and the driver/passenger may take measures at own discretion in this case.

Step 11: If the driver agrees on the authorization request, the second submodule of the ADS may execute the second driving policy. Specifically, the second submodule of the ADS may control the autonomous driving vehicle to stop on a roadside, turn on a hazard warning signal light, establish communication with a medical institution, call for a rescue, notify the driver/passenger of estimated time at which a rescue arrives, and the like.

It can be learned from the foregoing steps that the example of the autonomous driving method provided in this embodiment of this application also has the following advantages:

(1) A requirement of "first aid platinum 10 minutes" is fully considered. In a scenario related to a heart rate, even if the health level of the driver/passenger is an abnormality level, the driver/passenger is still conscious. The ADS needs to first query about intention of the driver/passenger before executing the second driving policy, for example, using an in-vehicle communication device (for example, a T-box) to call for help or call for an emergency medical resource, because if error reports are frequent, user experience is poor and the autonomous driving service that is being executed is frequently degraded. In this way, the intention of the driver/passenger is respected, and occasional indeterminate error reporting of the monitoring device can be avoided. In addition, time for discovering a health problem is advanced (because the driver/passenger may not perceive obvious discomfort if a mild abnormality occurs), so that advance detection and timely handling are implemented. In this way, user experience is desirable, and health of the driver/passenger is ensured. This reduces an occurrence rate of traffic accidents, and also brings huge social benefits.

(2) Continuity of the autonomous driving service is ensured. If a physical status of the driver/passenger is recovered (considering that the driver/passenger has carried first-aid medicine to be taken), a takeover capability level gradually decreases (for example, decreases from a level 3 to a level 2). In addition, if the ODD of the autonomous driving service is normal except a takeover capability indicator of the driver/passenger, the ADS controls the autonomous driving service to be recovered when the real-time physiological data of the driver/passenger is restored to fall within the health physiological data range.

(3) Responsibilities between the person and the vehicle are clear. The ADS may record, as the event log, all health-related data and operations during a period when the real-time physiological data is abnormal, and periodically (for example, every five minutes) report the event log to the cloud end corresponding to the autonomous driving vehicle for backup.

In addition, it can be learned from the example corresponding to FIG. 6A and FIG. 6B and the example corresponding to FIG. 7A and FIG. 7B that, the example of the autonomous driving method provided in the embodiment corresponding to FIG. 7A and FIG. 7B differs from the example of the autonomous driving method corresponding to FIG. 6A and FIG. 6B mainly in the following two aspects:

(1) In the case of the level L3, theoretically, the driver/passenger can take over the vehicle control right at any time. Therefore, in this case, the first driving policy includes making the ADS invariably occupy the vehicle control right. However, in the case of the level L4 or the level L5, the driver/passenger has no obligation or approach to take over the vehicle. Therefore, in this case, the first driving policy does not involve a handover of the vehicle control right.

(2) In the case of the level L3, the driver/passenger has greater discourse power. Therefore, the ADS may query about the intention of the driver/passenger in advance in execution of each step of the second driving policy. For example, when the driver/passenger accepts the authorization request, if the health level of the driver/passenger is a mild abnormality, the ADS may plan a route between a medical institution closest to the ADS and the ADS, and re-send an authorization request "the route to the nearest medical institution has been planned, whether to go". If the driver/passenger agrees to go, the ADS may control the autonomous driving vehicle to go to the medical institution. However, in the case of the level L4 or the level L5, the driver/passenger has no obligation or approach to take over the vehicle. Therefore, after the ADS sends an authorization request when the real-time physiological data is not restored to fall within the health physiological data range within the second preset duration, if the driver/passenger accepts the authorization request, the ADS directly executes the second driving policy, and subsequently does not query about the intention of the driver/passenger. For example, it is assumed that the specified second driving policy is "planning a traveling path between the autonomous driving vehicle and a nearest medical institution and going, and requesting the nearest medical institution to arrange an emergency medical treatment channel". Then, when the driver/passenger accepts the authorization request, the ADS directly controls the autonomous driving vehicle to plan the traveling path between the autonomous driving vehicle and the nearest medical institution and go, and requests, by using a communication device on the autonomous driving vehicle, the nearest medical institution to arrange an emergency medical treatment channel. In some implementations of this application, the ADS may broadcast an execution status of the second driving policy to the driver/passenger in real time.

Figure 8:
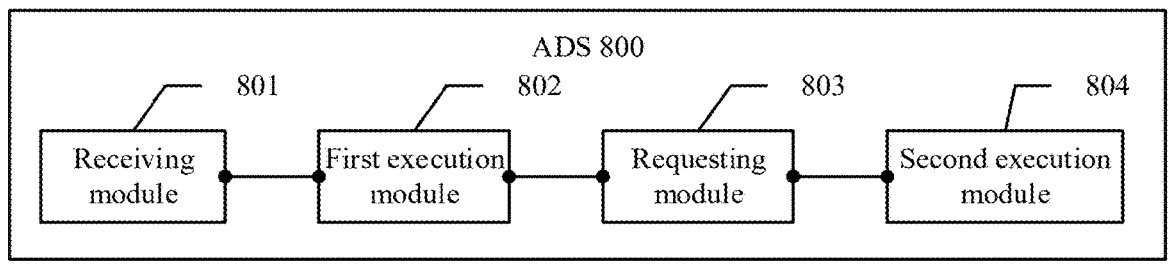
FIG. 8 is a schematic diagram of a structure of an ADS according to an embodiment of this application.

Based on the embodiments corresponding to FIG. 5 to FIG. 7A and FIG. 7B, for better implementation of the foregoing solutions in embodiments of this application, the following further provides related devices configured to implement the foregoing solutions. For details, refer to FIG. 8. FIG. 8 is a schematic diagram of a structure of an ADS 800 according to an embodiment of this application. The ADS 800 may specifically include a receiving module 801 and a first execution module 802. The receiving module 801 is configured to receive real-time physiological data of a driver/passenger that is collected by a monitoring device; and the first execution module 802 is configured to: when a difference between the real-time physiological data and a health physiological data range is greater than a preset value, and a duration in which the real-time physiological data deviates from the health physiological data range is greater than a first preset duration (for example, three minutes), degrade an autonomous driving service that is being executed by an autonomous driving vehicle, and execute a first driving policy based on the difference and the duration, where the health physiological data range is an applicable range added to an ODD in advance, and the ODD is deployed on the ADS.

In the implementation of this application, the health physiological data range as the applicable range of the ODD is newly added to the ODD. When the real-time physiological data of the driver/passenger deviates from the range for specific duration, the ADS determines that health of the driver/passenger is abnormal, and executes the corresponding first driving policy based on a deviation degree and the duration, to handle a sudden health accident of the driver/passenger in a timely manner, and reduce an occurrence rate of traffic accidents.

In a possible design, the ADS 800 further includes a requesting module 803 and a second execution module 804. The requesting module 803 is configured to send an authorization request when the real-time physiological data is not restored to fall within the health physiological data range within a second preset duration (for example, within eight minutes); and the second execution module 804 is configured to execute a second driving policy when the driver/passenger accepts the authorization request.

In the implementation of this application, the second driving policy is essentially an upgrade of an original risk mitigation strategy. For the original risk mitigation strategy, regardless of a specific autonomous driving level, when the ADS cannot perform a dynamic driving task or the driver/passenger cannot take over a dynamic driving task, a final objective of the risk mitigation strategy is "stopping the vehicle", that is, only vehicle safety in a narrow sense is considered. However, in embodiments of this application, for the second driving policy, in addition to considering stopping the vehicle, more efforts may be made in the vehicle in an actual situation, including but not limited to measures such as calling for help, organizing a rescue, requesting to arrange an emergency access, and reserving a medical resource.

In a possible design, the second driving policy includes at least one of the following policies: any one or more of the following: stopping on a roadside, calling for a rescue, establishing a communication connection to a medical institution, planning a traveling path between the autonomous driving vehicle and the medical institution, reserving a medical resource, and requesting to arrange an emergency medical treatment channel.

In the implementation of this application, several representation forms of the second driving policy are specifically described, and a requirement of "first aid platinum 10 minutes" is fully considered. In other words, time for discovering a health problem is advanced, so that advance detection and timely handling are implemented. In this way, user experience is desirable, and health of the driver/passenger is ensured. This reduces an occurrence rate of traffic accidents, and also brings huge social benefits.

In a possible design, if an autonomous driving level is L4 or L5, the first execution module 802 is specifically configured to: determine a health level of the driver/passenger based on the difference and the duration; and execute the first driving policy based on the health level when determining that the health level is a mild abnormality, where the first driving policy includes any one or more of: controlling, by the ADS, the autonomous driving vehicle to decrease a speed to be lower than a preset speed (for example, lower than 60 km/h), travel on a roadside, and turn on a hazard warning signal light.

The implementation of this application describes how the first driving policy is when the health level of the driver/passenger is a mild abnormality if the autonomous driving level is the level L4 or the level L5. To be specific, the health level is determined based on the difference between the real-time physiological data and the health physiological data range and the deviation duration, and different first driving policies are used based on different health levels. This is more pertinent to specific cases.

In a possible design, the first execution module 802 is further specifically configured to: execute the first driving policy based on the health level when determining that the health level is a severe abnormality, where the first driving policy includes any one or more of: controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and unlock a central door lock.

The implementation of this application describes how the first driving policy is when the health level of the driver/passenger is a severe abnormality if the autonomous driving level is the level L4 or the level L5. To be specific, the health level is determined based on the difference between the real-time physiological data and the health physiological data range and the deviation duration, and different first driving policies are used based on different health levels. This is more pertinent to specific cases.

In a possible design, if an autonomous driving level is L3, the first execution module 802 is specifically configured to: make the ADS invariably occupy control permission of the autonomous driving vehicle; determine a health level of the driver/passenger based on the difference and the duration; and execute the first driving policy based on the health level when determining that the health level is a mild abnormality, where the first driving policy includes any one or more of: controlling, by the ADS, the autonomous driving vehicle to decrease a speed to be lower than a preset speed (for example, lower than 60 km/h), travel on a roadside, and turn on a hazard warning signal light.

The implementation of this application provides the following description: In addition to making the ADS invariably occupy the control right of the autonomous driving vehicle, the first driving policy may be further the any one or more of: controlling, by the ADS, the autonomous driving vehicle to decrease the speed to be lower than the preset speed, travel on the roadside, and turn on the hazard warning signal light, when the health level of the driver/passenger (the driver/passenger is actually a driver in a driving seat in the case of the level L3) is the mild abnormality if the autonomous driving level is L3. To be specific, the health level is determined based on the difference between the real-time physiological data and the health physiological data range and the deviation duration, and different first driving policies are used based on different health levels. This is more pertinent to specific cases. Moreover, in this embodiment of this application, the driver/passenger has a right to take over the vehicle control right only when the health level of the driver/passenger is a normal level; otherwise, the vehicle control right cannot be handed over to the driver/passenger. This avoids a vehicle risk and a personal safety problem caused because the driver/passenger actually has no takeover capability in a specific time period due to a physical health problem.

In a possible design, if the autonomous driving level is the level L3, the first execution module 802 is further specifically configured to: execute the first driving policy based on the health level when determining that the health level is a severe abnormality, where the first driving policy includes any one or more of: controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and unlock a central door lock.

The implementation of this application provides the following description: In addition to making the ADS invariably occupy the control right of the autonomous driving vehicle, the first driving policy may be further the any one or more of: controlling the autonomous driving vehicle to slowly decrease the speed to zero, stop on the roadside, turn on the hazard warning signal light, run at the idle speed, turn on the external circulation of the vehicle, turn on the internal circulation of the vehicle, set the in-vehicle target temperature, and unlock the central door lock, when the health level of the driver/passenger (the driver/passenger is actually the driver in the driving seat in the case of the level L3) is the severe abnormality if the autonomous driving level is L3. To be specific, the health level is determined based on the difference between the real-time physiological data and the health physiological data range and the deviation duration, and different first driving policies are used based on different health levels. This is more pertinent to specific cases. Moreover, in this embodiment of this application, the driver/passenger has a right to take over the vehicle control right only when the health level of the driver/passenger is a normal level; otherwise, the vehicle control right cannot be handed over to the driver/passenger. This avoids a vehicle risk and a personal safety problem caused because the driver/passenger actually has no takeover capability in a specific time period due to a physical health problem.

In a possible design, the first execution module is further configured to: control the autonomous driving vehicle to resume execution of the autonomous driving service when the real-time physiological data is restored to fall within the health physiological data range within the second preset duration (for example, within 8 minutes).

In the implementation of this application, regardless of a specific autonomous driving level, when the real-time physiological data collected by the monitoring device is restored to fall within the health physiological data range within the second preset duration, it indicates that the health status of the driver/passenger is temporarily restored. In this case, the ADS may control the autonomous driving vehicle to recover the degraded autonomous driving service. This improves user experience.

In a possible design, the first execution module 802 is further configured to generate an event log based on the real-time physiological data, where the event log is used to record the real-time physiological data and an operation of the ADS during a period when the real-time physiological data deviates from the health physiological data range; and periodically report the event log to a cloud server corresponding to the autonomous driving vehicle.

In the implementation of this application, the ADS may further generate an event log based on the real-time physiological data, where the event log is used to record abnormal real-time physiological data and a series of subsequent operations of the ADS during a period when the real-time physiological data deviates from the health physiological data range; and periodically report the event log to the cloud server corresponding to the autonomous driving vehicle. This is convenient to distinguish responsibilities between the person and the vehicle.

In a possible design, the real-time physiological data includes at least one type of the following physiological data: real-time blood pressure, a real-time heart rate, real-time blood oxygen, a real-time body temperature, a premature heartbeat, atrial fibrillation, and other real-time physiological data of the driver/passenger, provided that the physiological data can be collected by the monitoring device and can reflect the health status of the driver/passenger. This is not specifically limited herein.

In the implementation of this application, several common forms of the real-time physiological data are described, and are selective and flexible.

It should be noted that content such as information exchange and execution processes between the modules/units in the ADS 800 in the embodiment corresponding to FIG. 8 is based on a same concept as that in the method embodiments corresponding to FIG. 5 to FIG. 7A and FIG. 7B in this application. For specific content, refer to descriptions in the foregoing method embodiments of this application. Details are not described herein again.

Figure 9:
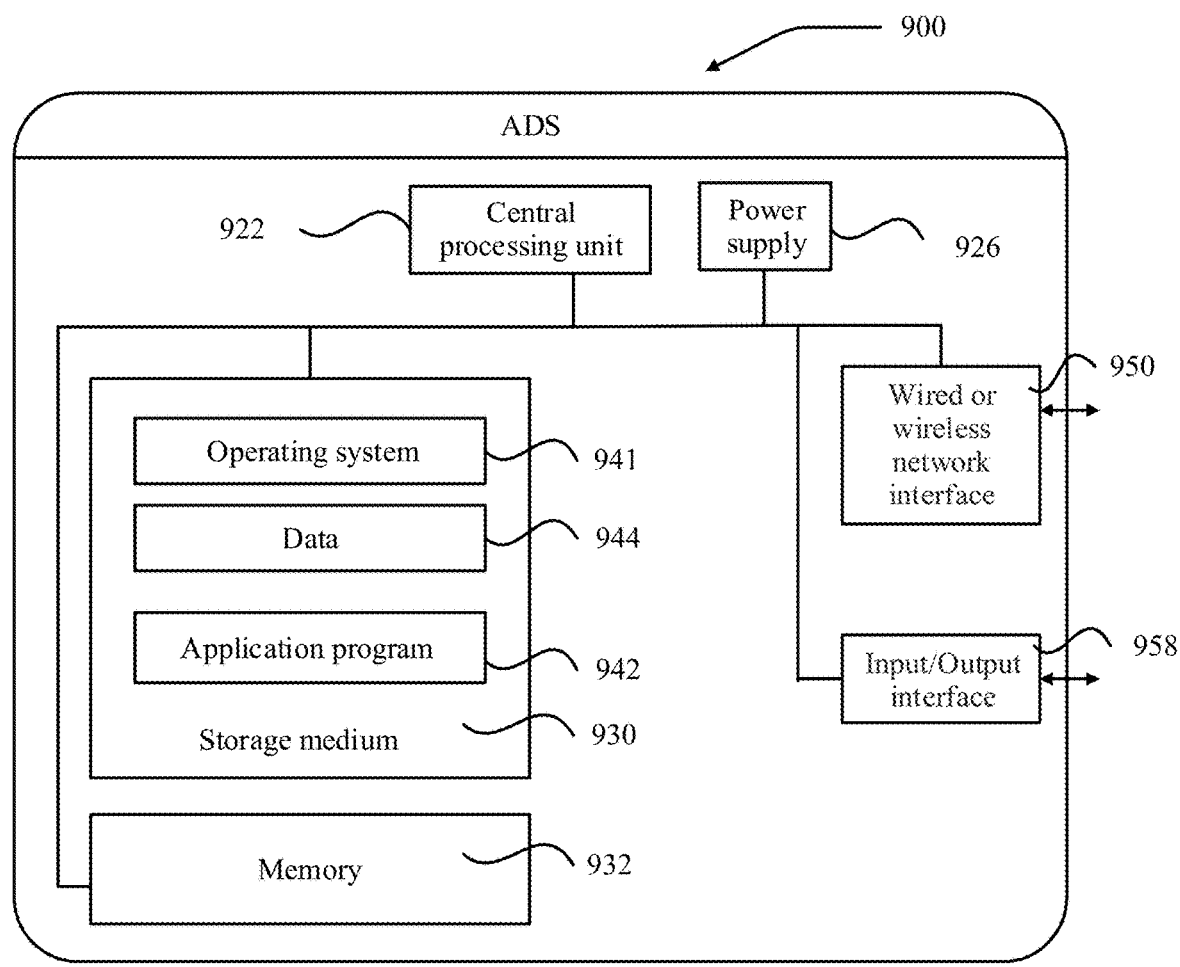
FIG. 9 is another schematic diagram of a structure of an ADS according to an embodiment of this application.

An embodiment of this application further provides an ADS. FIG. 9 is a schematic diagram of a structure of an ADS according to an embodiment of this application. For case of description, only parts related to this embodiment of this application are described, and specific technical details are not disclosed. For details, refer to the method parts in embodiments of this application. The modules of the ADS described in the embodiment corresponding to FIG. 8 may be deployed on the ADS 900, and is configured to implement a function of the ADS in the embodiment corresponding to FIG. 8. Specifically, the ADS 900 is implemented by one or more servers. The ADS 900 may vary greatly due to different configurations or performance, and may include one or more central processing units (cCPU) 922 and a memory 932, one or more storage media 930 (for example, one or more mass storage devices) storing an application program 942 or data 944. The memory 932 and the storage medium 930 may be temporary storage or permanent storage. The program stored in the storage medium 930 may include one or more modules (not shown in the figure), where each module may include a series of instruction operations for the ADS 900. Further, the central processing unit 922 may be set to communicate with the storage medium 930, and execute, in the ADS 900, the series of instruction operations in the storage medium 930.

The ADS 900 may further include one or more power supplies 926, one or more wired or wireless network interfaces 950, one or more input/output interfaces 958, and/or one or more operating systems 941, for example, Windows Server™, Mac OS X™, Unix™, Linux™, or FreeBSD™.

In this embodiment of this application, the steps performed by the ADS in the embodiments corresponding to FIG. 5 to FIG. 7A and FIG. 7B may be implemented based on the structure shown in FIG. 9. Details are not described herein again.

In addition, it should be noted that the described apparatus embodiments are merely examples. The units described as separate parts may or may not be physically separate. Parts displayed as units may or may not be physical units, and may be located in one position or distributed on a plurality of network units. Some or all of the modules may be selected depending on an actual requirement to achieve the objectives of the solutions in embodiments. In addition, in the accompanying drawings of the apparatus embodiments provided in this application, connection relationships between modules indicate that the modules have communication connections to each other, which may be specifically implemented as one or more communication buses or signal cables.

Based on the descriptions of the foregoing implementations, a person skilled in the art can clearly understand that this application may be implemented by using software in addition to necessary commodity hardware, and certainly may be alternatively implemented by using dedicated hardware, including a dedicated integrated circuit, a dedicated CPU, a dedicated memory, a dedicated component, and the like. Generally, any function implemented by a computer program can be easily implemented by using corresponding hardware. Moreover, specific hardware structures used to implement a same function may be of various forms, for example, in forms of an analog circuit, a digital circuit, or a dedicated circuit. However, as for this application, software program implementation is a better implementation in most cases. Based on such an understanding, the technical solutions of this application essentially or the part contributing to the prior art may be implemented in a form of a software product. The computer software product is stored in a readable storage medium, such as a floppy disk, a USB flash drive, a removable hard disk, a read-only memory (ROM), a random access memory (RAM), a magnetic disk, or an optical disc of a computer, and includes several instructions for instructing a computer device (which may be a personal computer, a training device, a network device, or the like) to perform the methods described in embodiments of this application.

All or some of the foregoing embodiments may be implemented by using software, hardware, firmware, or any combination thereof. When software is used to implement the foregoing embodiments, the foregoing embodiments may be implemented completely or partially in a form of a computer program product.

The computer program product includes one or more computer instructions. When the computer program instructions are loaded and executed on a computer, the procedures or functions according to embodiments of this application are completely or partially generated. The computer may be a general-purpose computer, a dedicated computer, a computer network, or another programmable apparatus. The computer instructions may be stored in a computer-readable storage medium or may be transmitted from a computer-readable storage medium to another computer-readable storage medium. For example, the computer instructions may be transmitted from a website, computer, training device, or data center to another website, computer, training device, or data center in a wired (for example, a coaxial cable, an optical fiber, or a digital subscriber line) or wireless (for example, infrared, radio, or microwave) manner. The computer-readable storage medium may be any usable medium accessible to a computer, or a data storage device, such as a training device or a data center, integrating one or more usable media. The usable medium may be a magnetic medium (for example, a floppy disk, a hard disk, or a magnetic tape), an optical medium (for example, a digital video disc (digital video disc, DVD)), a semiconductor medium (for example, a solid state disk (SSD)), or the like.

What is claimed is:

1. An autonomous driving method performed by an autonomous driving system (ADS), the method comprising:
   obtaining real-time physiological data of a vehicle occupant collected by a monitoring device;
   comparing the obtained real-time physiological data with a healthy physiological data range, the healthy physiological data range being an applicable range added to an operational design domain (ODD) deployed on the ADS;
   determining that a difference between the real-time physiological data and a healthy physiological data range exceeds a preset value and that a duration for which the real-time physiological data deviates from the healthy physiological data range exceeds a preset duration;
   degrading, in response to the determining, an autonomous driving service being executed by an autonomous vehicle;
   executing a first driving policy based on the determined difference between the real-time physiological data and the healthy physiological data range and the determined duration for which the real-time physiological data deviates from the healthy physiological data range; and
   after executing the first driving policy:
   determining that the real-time physiological data does not return to the healthy physiological data range within a second preset duration,
   sending, in response to the determining that the real-time physiological data does not return to the healthy physiological data range within the second preset duration, an authorization request, and
   executing a second driving policy in response to the vehicle occupant or another vehicle occupant accepting the authorization request.

2. The method according to claim 1, wherein the second driving policy comprises:
   stopping on a roadside, calling for a rescue, establishing a communication connection to a medical institution, planning a traveling path between the autonomous driving vehicle and the medical institution, reserving a medical resource, and/or requesting to arrange an emergency medical treatment channel.

3. The method according to claim 1, wherein an autonomous driving level is L4 or L5, and the step of executing the first driving policy based on the determined difference between the real-time physiological data and the healthy physiological data range and the determined duration for which the real-time physiological data deviates from the healthy physiological data range comprises:
   determining a health level of the vehicle occupant based on the determined difference between the real-time physiological data and the healthy physiological data range and the determined duration for which the real-time physiological data deviates from the healthy physiological data range; and
   executing the first driving policy based on the health level when determining that the health level is a mild abnormality, wherein the first driving policy comprises controlling, by the ADS, the autonomous driving vehicle to: decrease a speed to be lower than a preset speed, travel on a roadside, and/or turn on a hazard warning signal light.

4. The method according to claim 3, further comprising:
   executing the first driving policy based on the health level when determining that the health level is a severe abnormality, wherein the first driving policy comprises controlling, by the ADS, the autonomous driving vehicle to: slowly decrease the speed to zero, stop on a roadside, turn on a hazard warning signal light, run at an idle speed, turn on an external circulation of the vehicle, turn on an internal circulation of the vehicle, set an in-vehicle target temperature, and/or unlock a central door lock.

5. The method according to claim 1, wherein an autonomous driving level is L3, and the step of executing the first driving policy based on the determined difference between the real-time physiological data and the healthy physiological data range and the determined duration for which the real-time physiological data deviates from the healthy physiological data range comprises:
    making the ADS invariably occupy control permission of the autonomous driving vehicle;
    determining a health level of the vehicle occupant based on the determined difference between the real-time physiological data and the healthy physiological data range and the determined duration for which the real-time physiological data deviates from the healthy physiological data range; and
    executing the first driving policy based on the health level when determining that the health level is a mild abnormality, wherein the first driving policy comprises controlling, by the ADS, the autonomous driving vehicle to: decrease a speed to be lower than a preset speed, travel on a roadside, and/or turn on a hazard warning signal light.

6. The method according to claim 5, further comprising:
    executing the first driving policy based on the health level when determining that the health level is a severe abnormality, wherein the first driving policy comprises controlling, by the ADS, the autonomous driving vehicle to: slowly decrease the speed to zero, stop on a roadside, turn on a hazard warning signal light, run at an idle speed, turn on an external circulation of the vehicle, turn on an internal circulation of the vehicle, set an in-vehicle target temperature, and/or unlock a central door lock.

7. The method according to claim 1, wherein after the step of executing the first driving policy based on the determined difference between the real-time physiological data and the healthy physiological data range and the determined duration for which the real-time physiological data deviates from the healthy physiological data range, the method further comprises:
    controlling the autonomous driving vehicle to resume execution of the autonomous driving service when the real-time physiological data is restored to fall within the health physiological data range within the second preset duration.

8. The method according to claim 1, further comprising:
    generating an event log based on the real-time physiological data, wherein the event log records the real-time physiological data and an operation of the ADS during a period when the real-time physiological data deviates from the healthy physiological data range; and
    periodically reporting the event log to a cloud server corresponding to the autonomous driving vehicle.

9. The method according to claim 1, wherein the real-time physiological data comprises:
    real-time blood pressure, a real-time heart rate, real-time blood oxygen, and/or a real-time body temperature of the vehicle occupant.

10. An autonomous driving system (ADS) comprising:
    a memory storing executable instructions; and
    a processor configured to execute the executable instructions so as to:
    obtain real-time physiological data of a vehicle occupant collected by a monitoring device,
    compare the obtained real-time physiological data with a healthy physiological data range, the healthy physiological data range being an applicable range added to an operational design domain (ODD) deployed on the ADS;
    determine that a difference between the real-time physiological data and a healthy physiological data range exceeds a preset value and that a duration for which the real-time physiological data deviates from the healthy physiological data range exceeds a preset duration;
    degrade, in response to the determining, an autonomous driving service being executed by an autonomous vehicle, and
    execute a first driving policy based on the determined difference between the real-time physiological data and the healthy physiological data range and the determined duration for which the real-time physiological data deviates from the healthy physiological data range; and
    after executing the first driving policy:
    determine that the real-time physiological data does not return to the healthy physiological data range within a second preset duration,
    send, in response to the determining that the real-time physiological data does not return to the healthy physiological data range within the second preset duration, an authorization request, and
    execute a second driving policy in response to the vehicle occupant or another vehicle occupant accepting the authorization request.

11. The ADS according to claim 10, wherein the second driving policy comprises:
    stopping on a roadside, calling for a rescue, establishing a communication connection to a medical institution, planning a traveling path between the autonomous driving vehicle and the medical institution, reserving a medical resource, and/or requesting to arrange an emergency medical treatment channel.

12. The ADS according to claim 10, wherein an autonomous driving level is L4 or L5, and the processor is configured to execute the first driving policy by:
    determining a health level of the driver/passenger based on the determined difference between the real-time physiological data and the healthy physiological data range and the determined duration for which the real-time physiological data deviates from the healthy physiological data range; and
    executing the first driving policy based on the health level when determining that the health level is a mild abnormality, wherein the first driving policy comprises controlling, by the ADS, the autonomous driving vehicle to: decrease a speed to be lower than a preset speed, travel on a roadside, or turn on a hazard warning signal light.

13. The ADS according to claim 12, wherein the processor is further configured to execute the executable instructions to:
    execute the first driving policy based on the health level when determining that the health level is a severe abnormality, wherein the first driving policy comprises controlling, by the ADS, the autonomous driving vehicle to slowly decrease the speed to zero, stop on a roadside, turn on a hazard warning signal light, run at an idle speed, turn on an external circulation of the vehicle, turn on an internal circulation of the vehicle, set an in-vehicle target temperature, and/or unlock a central door lock.

14. The ADS according to claim 10, wherein an autonomous driving level is L3, and the processor is configured to execute the first driving policy by:
    making the ADS invariably occupy control permission of the autonomous driving vehicle;
    determining a health level of the driver/passenger based on the determined difference between the real-time physiological data and the healthy physiological data range and the determined duration for which the real-time physiological data deviates from the healthy physiological data range; and executing the first driving policy based on the health level when determining that the health level is a mild abnormality, wherein the first driving policy comprises controlling, by the ADS, the autonomous driving vehicle to: decrease a speed to be lower than a preset speed, travel on a roadside, or turn on a hazard warning signal light.

15. The ADS according to claim 14, wherein the processor is further configured to execute the executable instructions to:

execute the first driving policy based on the health level when determining that the health level is a severe abnormality, wherein the first driving policy comprises controlling, by the ADS, the autonomous driving vehicle to: slowly decrease the speed to zero, stop on a roadside, turn on a hazard warning signal light, run at an idle speed, turn on an external circulation of the vehicle, turn on an internal circulation of the vehicle, set an in-vehicle target temperature, and/or unlock a central door lock.

16. The ADS according to claim 10, wherein the processor is further configured to execute the executable instructions to:

control the autonomous driving vehicle to resume execution of the autonomous driving service when the real-time physiological data is restored to fall within the health physiological data range within the second preset duration.

17. The ADS according to claim 10, wherein the processor is further configured to execute the executable instructions to:

generate an event log based on the real-time physiological data, wherein the event log records the real-time physiological data and an operation of the ADS during a period when the real-time physiological data deviates from the health physiological data range; and periodically report the event log to a cloud server corresponding to the autonomous driving vehicle.

18. The ADS according to claim 10, wherein the real-time physiological data comprises: real-time blood pressure, a real-time heart rate, real-time blood oxygen, or a real-time body temperature of the vehicle occupant.

* * * * *